United States Patent
El-Zefzafy et al.

(10) Patent No.: US 10,551,367 B2
(45) Date of Patent: Feb. 4, 2020

(54) GEOCHEMICAL WATER ANALYSIS ELEMENT CONCENTRATION PREDICTION FOR OILFIELD WATERS

(71) Applicant: Saudi Arabian Oil Company, Dhahran (SA)

(72) Inventors: Ibrahim Mohamed El-Zefzafy, Udhailiyah (SA); Mohammed Hassan Al Hanabi, Safwa (SA)

(73) Assignee: Saudi Arabian Oil Company, Dhahran (SA)

( * ) Notice: Subject to any disclaimer, the term of this patent is extended or adjusted under 35 U.S.C. 154(b) by 523 days.

(21) Appl. No.: 14/750,775

(22) Filed: Jun. 25, 2015

(65) Prior Publication Data
US 2016/0377585 A1   Dec. 29, 2016

(51) Int. Cl.
| | | |
|---|---|---|
| *G01N 33/18* | (2006.01) | |
| *G01V 3/18* | (2006.01) | |
| *G01V 3/38* | (2006.01) | |

(52) U.S. Cl.
CPC ............... *G01N 33/18* (2013.01); *G01V 3/18* (2013.01); *G01V 3/38* (2013.01)

(58) Field of Classification Search
CPC .... G01N 33/18; G01N 33/1886; E21B 49/08; E21B 49/081; E21B 2049/085; E21B 43/00; E21B 47/10; G01V 3/18
See application file for complete search history.

(56) References Cited

U.S. PATENT DOCUMENTS

| | | |
|---|---|---|
| 3,399,037 A | 8/1968 | Eckfeldt |
| 3,537,820 A | 11/1970 | Markant et al. |
| 3,916,997 A | 11/1975 | Douglas et al. |
| 4,434,233 A | 2/1984 | Bzdula |
| 4,801,551 A | 1/1989 | Byers et al. |
| 5,497,321 A | 3/1996 | Ramakrishnan et al. |
| 5,504,009 A | 4/1996 | Ohmi et al. |
| 5,668,369 A | 9/1997 | Oraby |
| 5,896,926 A * | 4/1999 | Hama ................. E02D 1/06 166/250.07 |
| 6,195,092 B1 | 2/2001 | Dhond et al. |

(Continued)

FOREIGN PATENT DOCUMENTS

WO   2010/012093   2/2010

OTHER PUBLICATIONS

Bilhartz, "A standardized Method of Monitoring Water Quality in Sub-Surface Injection System", Society of Petroleum Engineers, SPE1793, Copyright 1967, 11 pages.

(Continued)

*Primary Examiner* — Gene N Auduong
(74) *Attorney, Agent, or Firm* — Fish & Richardson P.C.

(57) ABSTRACT

A first wellhead fluid sample is collected from a petroleum well. Multiple geochemical water analysis (GWA) tests are preformed to form GWA water analysis data. The GWA tests determine physical properties of, and one or more geochemical water element (GWE) concentration values associated with, the first wellhead fluid sample. Correlation data associated with the GWA water analysis data is determined. A second wellhead fluid sample is collected from the petroleum well and only a water conductivity analysis is performed on the second wellhead fluid sample to determine water conductivity data.

17 Claims, 16 Drawing Sheets

(56) References Cited

U.S. PATENT DOCUMENTS

| | | | |
|---|---|---|---|
| 8,268,629 | B2 | 9/2012 | Coleman et al. |
| 8,838,390 | B1 | 9/2014 | Selman et al. |
| 2006/0163467 | A1* | 7/2006 | Raghuraman ....... E21B 47/1015 250/259 |
| 2007/0203681 | A1 | 8/2007 | Eyvazzadeh et al. |
| 2007/0257684 | A1 | 11/2007 | Essich |
| 2011/0040501 | A1* | 2/2011 | Martin ................... E21B 47/10 702/45 |
| 2012/0114089 | A1 | 5/2012 | Potyrallo et al. |
| 2012/0201929 | A1 | 8/2012 | Guy et al. |
| 2013/0328579 | A1 | 12/2013 | Whitehead et al. |
| 2016/0334343 | A1* | 11/2016 | Hurlimann ............. G01N 33/18 |

OTHER PUBLICATIONS

Zaporozec, "Graphical Interpretation of Water-Quality Data", vol. 10, No. 2, Ground Water, Mar.-Apr. 1972, 12 pages.

Joarder et al., "Regression Analysis of Ground Water Quality Data of Sunamganj District, Bangladesh", International Journal of Environmental Research, ISSN: 1735-6865, pp. 291-296.

Capelle, "Water-Analysis Diagrams—Kansas Oil-Field Brines", Apr. 1956, pp. 238-248.

International Search Report and Written Opinion of the International Searching Authority issued in International Application No. PCT/US2015/057485 dated Mar. 8, 2016; 12 pages.

Al-Sheri, A. et al.; "Successfule Optimization of Utilizing Multiphasing Flow Meters (MPFMs) for Multiple Wells with a Wide Range of Fluid Properties in South Ghawar"; SPE International; May 19, 2013.

European Communication under Rule 71(3) EPC issued in European Application No. 15790775.9 dated Feb. 19, 2019, 56 pages.

Gulf Cooperative Council Examination Report issued in GCC Application No. GCC 2016-31042 dated Jun. 17, 2018, 5 pages.

* cited by examiner

Geo-Chemical Water Analysis Report

Page 1 of 2

| WELL NAME | AQFR/ RSVR | SAMPLE DATE YYYY/MM/DD | TIME/ REMARKS | NA⁺ | CA | MG | SO4 | CL | CO3 | HCO3 | TDS | PH | SP GR | LAB | TYP | SRC | QLTY | VAL |
|---|---|---|---|---|---|---|---|---|---|---|---|---|---|---|---|---|---|---|
| UTMN | 50 ARBD | 1982/03/29 | WATER = 53% | 23300 | 7200 | 1340 | 660 | 50300 | | 320 | 82,120 | 6.8 | 1.0677 | UN | F | | D | G |
| UTMN | 50 ARBD | 1983/05/12 | WATER=40% | 24500 | 8490 | 1190 | 930 | 55500 | | 460 | 91,160 | 7.2 | 1.0673 | UN | F | | D | F |
| UTMN | 50 ARBD | 1984/01/16 | | 18300 | 5660 | 1230 | 630 | 41000 | | 600 | 67,420 | 7.1 | 1.0686 | UN | F | | D | F |
| UTMN | 50 ARBD | 1984/07/18 | WTR=15% | 19400 | 5900 | 780 | 740 | 42050 | | 180 | 69,000 | 6.9 | 1.0509 | UN | F | | D | G |
| UTMN | 50 ARBD | 1985/03/18 | | 17700 | 5740 | 840 | 530 | 39450 | | 200 | 64,410 | 6.8 | 1.0470 | UN | F | | D | F |
| UTMN | 50 ARBD | 1986/04/09 | WATER=40% | 16600 | 5800 | 920 | 770 | 37700 | 0 | 420 | 62,200 | 7.1 | 1.0342 | UN | F | WM | D | G |
| UTMN | 50 ARBD | 1987/06/08 | WATERCUT = 47% | 16100 | 4610 | 690 | 750 | 34300 | 0 | 500 | 56,900 | 7.1 | 1.0416 | UN | F | WM | G | G |
| UTMN | 50 ARBD | 1987/11/16 | MGL, SR = 246 MGL | 14700 | 5100 | 710 | 610 | 33100 | 0 | 360 | 54,600 | 7.5 | 1.0398 | UN | | WM | G | F |
| UTMN | 50 ARBD | 1988/06/25 | WATERCUT = 83 % | 15000 | 4260 | 750 | 850 | 32100 | 0 | 380 | 53,300 | 6.9 | 1.0398 | AB | F | WM | G | G |
| UTMN | 50 ARBD | 1989/06/17 | WATER CUT = 45.5 % | 13900 | 3960 | 710 | 980 | 29600 | 0 | 410 | 49,400 | 7.2 | 1.0364 | AB | F | WM | G | G |
| UTMN | 50 ARBD | 1989/07/17 | WATERCUT = 44% | 14700 | 3920 | 710 | 1060 | 30600 | 0 | 570 | 51,600 | 7.3 | 1.0379 | AB | F | WM | G | G |
| UTMN | 50 ARBD | 1990/08/12 | WATERCUT = 51 % | 15000 | 3580 | 630 | 1250 | 30200 | 0 | 380 | 51,100 | 7.3 | 1.0372 | AB | F | WM | G | G |
| UTMN | 50 ARBD | 1991/06/19 | | 14634 | 3600 | 700 | 835 | 30200 | 0 | 380 | 50,321 | 7.1 | 1.0369 | AB | F | | G | G |
| UTMN | 50 ARBD | 1991/07/17 | | 16147 | 3335 | 730 | 1130 | 31400 | 0 | 370 | 53,911 | 7.4 | 1.0385 | AB | | | G | G |
| UTMN | 50 ARBD | 1992/07/20 | | 14300 | 3850 | 640 | 920 | 29700 | 0 | 1170 | 49,390 | 7.7 | 1.0381 | AB | | | G | G |
| UTMN | 50 ARBD | 1992/07/29 | | 15500 | 3480 | 650 | 860 | 31200 | 0 | 24 | 52,400 | 7.4 | 1.0382 | AB | | | G | G |
| UTMN | 50 ARBD | 1992/08/15 | | 13900 | 3430 | 680 | 950 | 30000 | 0 | 500 | 50,700 | 7.5 | 1.0381 | AB | | | G | G |
| UTMN | 50 ARBD | 1993/07/14 | | 16200 | 3090 | 660 | 1150 | 31300 | 0 | 700 | 52,860 | 7.5 | 1.0370 | AB | | | G | G |
| UTMN | 50 ARBD | 1993/07/19 | | 15400 | 3440 | 690 | 1040 | 30700 | 0 | 510 | 51,960 | 7.5 | 1.0387 | AB | | | G | G |
| UTMN | 50 ARBD | 1994/01/02 | | 15800 | 3400 | 670 | 980 | 30900 | 0 | 690 | 52,600 | 7.8 | 1.0383 | AB | | | G | G |
| UTMN | 50 ARBD | 1995/10/01 | | 16700 | 4030 | 800 | 890 | 34300 | 0 | 465 | 57,237 | 7.8 | 1.0420 | AB | F | WM | G | G |
| UTMN | 100 ARBD | 1992/07/25 | | 40000 | 15500 | 2040 | 790 | 94400 | 0 | 240 | 153,600 | 6.9 | 1.1083 | AB | | | G | G |
| UTMN | 100 ARBD | 1992/07/27 | | 35500 | 14400 | 1860 | 500 | 85100 | 0 | 310 | 137,700 | 7.0 | 1.0950 | AB | | | G | G |
| UTMN | 100 ARBD | 1992/10/24 | | 23100 | 7685 | 1030 | 720 | 51600 | 0 | 220 | 84,400 | 7.4 | 1.0615 | AB | | | G | G |
| UTMN | 100 ARBD | 1992/11/17 | | 21000 | 6930 | 830 | 720 | 46450 | 0 | 350 | 76,300 | 7.3 | 1.0561 | AB | | | G | B |

FIG. 2

| Regression Equation | Adjusted $R^2$ value | t value | p value | F- value |
|---|---|---|---|---|
| Ca = -6.7 + 0.12336 EC | 0.869 | 3.17 | 0.002* | 100.06 |
| Mg = 19.26 + 0.01640 EC | 0.393 | 2.05 | 0.043** | 40.21 |
| Cl = 9.415 + 0.04740 EC | 0.644 | 2.54 | 0.013** | 60.48 |
| $NO_3$ = 4.014 + 0.00356 EC | 0.881 | 3.64 | 0.001* | 104.10 |
| TDS = 230.81 + 0.5252 EC | 0.780 | 1.71 | 0.090*** | 29.3 |
| $Fe^{Total}$ = 1.173 + 0.00274 EC | 0.471 | 2.15 | 0.034** | 46.10 |
| $HCO_3$ = 48.304 + 0.2976 EC | 0.911 | 11.20 | 0.000* | 125.47 |
| TH = 28.67 + 0.4568 EC | 0.510 | 3.32 | 0.001* | 22.05 |

302c

Step 2: Chart Selection

| No. | X-Axis | | Y-Axis | |
|---|---|---|---|---|
| 1 | TIME | 🔍 ☐ log scale | CL | 🔍 ☐ log scale |
| 2 | TDS | 🔍 ☐ log scale | COND | 🔍 ☐ log scale |
| 3 | CA | 🔍 ☐ log scale | MG | 🔍 ☐ log scale |
| 4 | COND | 🔍 ☐ log scale | NA | 🔍 ☐ log scale |

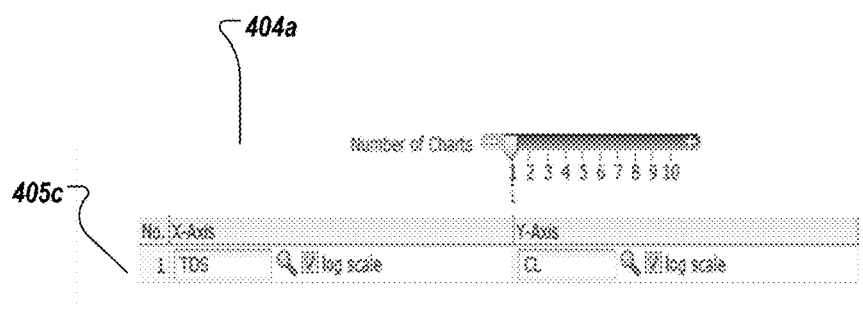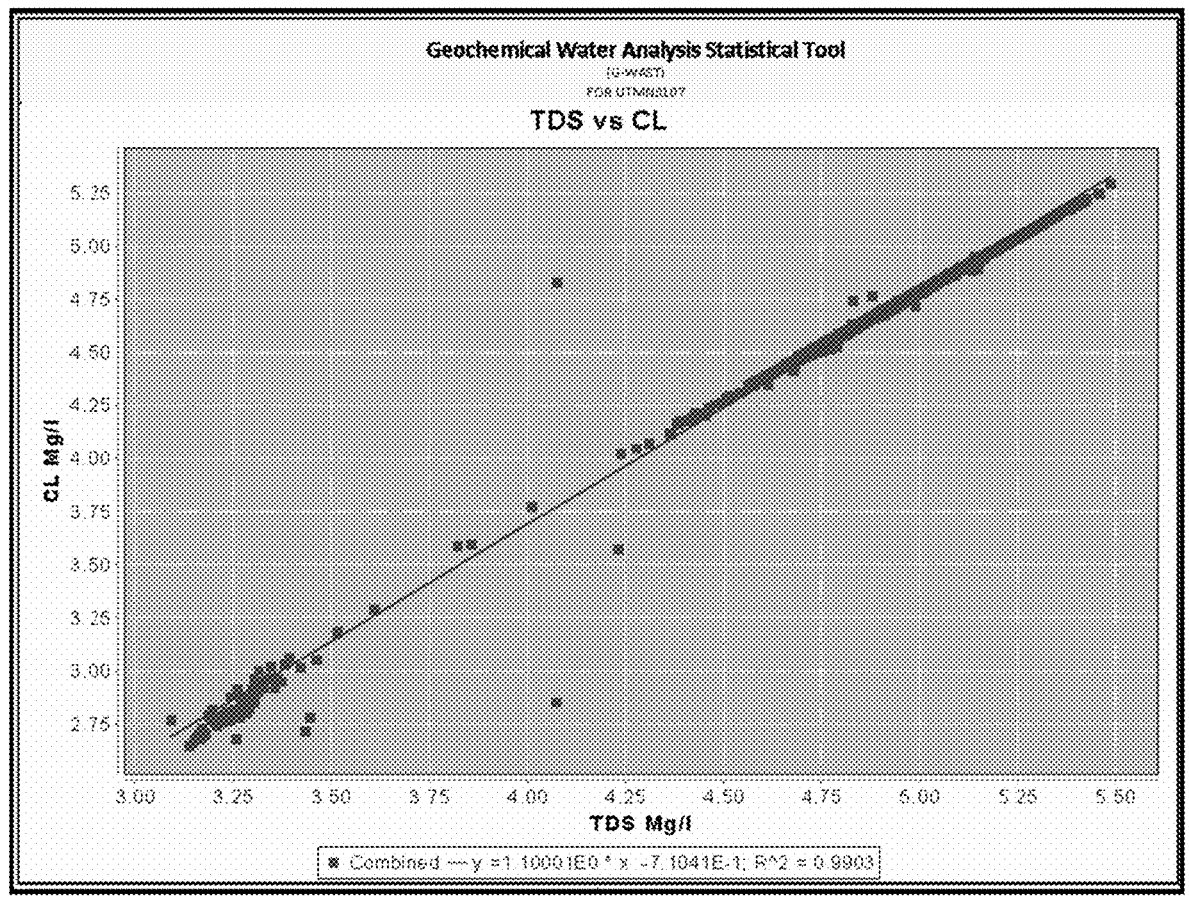
FIG. 4L

GEOCHEMICAL WATER ANALYSIS ELEMENT CONCENTRATION PREDICTION FOR OILFIELD WATERS

BACKGROUND

Geochemical water analysis (GWA) is a process used to derive water analysis data (e.g., physical and chemical properties) from water samples obtained from petroleum-producing wells as needed. GWA is typically expensive and requires multiple pieces of expensive lab equipment, technical expertise, and/or measurements of geochemical water element (GWE) concentrations (e.g., pH, water specific gravity, conductivity, sodium (Na), calcium (Ca), magnesium (Mg), chloride (Cl), sulfate, carbonate, bicarbonate, and/or total dissolved solids (TDSs)) of a particular water sample that make up the GWA water analysis data. The GWA water analysis data is then typically used for various purposes, including determining water breakthrough, casing leaks between different reservoirs, predicting precipitation of scale, monitoring sweep, water invasion, remedial actions, and/or other purposes. Changes over time in the GWE concentrations in water samples from one or more petroleum-producing wells can provide data useful to determine, among other things, petroleum resource trends and a reduction or expansion/further development of a petroleum field associated with a petroleum reservoir. The normal practice for comparing and validating available water analysis data is to leverage technical skill/expertise to numerically interpret GWA water analysis data—a difficult, inefficient, and time consuming process that does not leverage correlations and/or relationships that can be efficiently derived from available water analysis data and simple measurement of water conductivity. It is important to have an efficient and rapid ability to derive up-to-date data based on prior GWA water analysis data in order to be able to perform special analysis studies and to determine, for example and among other things, the above-mentioned petroleum resource trends and reduction or expansion/further development of the petroleum field associated with the petroleum reservoir.

SUMMARY

The present disclosure describes methods and systems, including computer-implemented methods, computer program products, and computer systems for predicting geochemical water elements (GWEs) in a water sample. In an implementation, a first wellhead fluid sample is collected from a petroleum well. Multiple geochemical water analysis (GWA) tests are preformed to form GWA water analysis data. The GWA tests determine physical properties of, and one or more geochemical water element (GWE) concentration values associated with, the first wellhead fluid sample. Correlation data associated with the GWA water analysis data is determined. A second wellhead fluid sample is collected from the petroleum well and only a water conductivity analysis is performed on the second wellhead fluid sample to determine water conductivity data.

In an implementation, a computer-implemented method includes collecting a first wellhead fluid sample from a petroleum well; performing multiple geochemical water analysis (GWA) tests to determine physical properties of and one or more geochemical water element (GWE) concentration values associated with the first wellhead fluid sample to form GWA water analysis data; determining correlation data associated with the GWA water analysis data; collecting a second wellhead fluid sample from the petroleum well; and performing only a water conductivity analysis on the second wellhead fluid sample to determine water conductivity data.

Other implementations of this aspect include corresponding computer systems, apparatuses, and computer programs recorded on one or more computer storage devices, each configured to perform the actions of the methods. A system of one or more computers can be configured to perform particular operations or actions by virtue of having software, firmware, hardware, or a combination of software, firmware, or hardware installed on the system that in operation causes the system to perform the actions. One or more computer programs can be configured to perform particular operations or actions by virtue of including instructions that, when executed by data processing apparatus, cause the apparatus to perform the actions.

The foregoing and other implementations can each optionally include one or more of the following features, alone or in combination.

A first aspect, combinable with the general implementation, wherein the GWA water analysis data and a backup of the GWA water analysis data are stored into persistent memory storage.

A second aspect, combinable with any of the previous aspects, wherein the GWA water analysis data includes at least one of pH, water specific gravity, conductivity, sodium (Na), calcium (Ca), magnesium (Mg), chloride (Cl), sulfate, carbonate, bicarbonate, or total dissolved solids (TDSs).

A third aspect, combinable with any of the previous aspects, comprising determining a current GWE value for a particular GWE using the determined correlation data and the determined water conductivity data.

A fourth aspect, combinable with any of the previous aspects, comprising using a geochemical water analysis statistical approach (G-WAST) application to determine correlations and relationships between the GWA water analysis data.

A fifth aspect, combinable with any of the previous aspects, wherein the G-WAST application provides functionality to permit multiple selected data criteria to be considered together for illustration and calculations.

A sixth aspect, combinable with any of the previous aspects, wherein an illustrated trendline can be manipulated to substantially fit within plotted data points of a scatterplot.

The subject matter described in this specification can be implemented in particular implementations so as to realize one or more of the following advantages. First, existing geochemical water analysis (GWA) water analysis data (e.g., for a particular petroleum well water sample, GWA water analysis data can include physical properties and GWE concentrations such as pH, water specific gravity, conductivity, sodium (Na), calcium (Ca), magnesium (Mg), chloride (Cl), sulfate, carbonate, bicarbonate, and/or total dissolved solids (TDSs)) can be leveraged by applications to help recover the cost of obtaining the original GWA water analysis data and to provide useful analysis and predictive functions. For example, a "geochemical water analysis statistical approach" ("G-WAST") application can be used to determine correlations and/or relationships between the GWEs associated with the existing GWA water analysis data and then graphically display the determined correlation and/or relationship results using a graphical technique associated with the G-WAST application. Second, in some implementations, a "water analysis elements concentration predication" ("WAECP") application can then be used to automatically predict GWEs (including TDSs) using the G-WAST-determined (established) correlations and/or relationships between the GWEs and only a water conductivity data value associated with a current water sample. Third, the use of the G-WAST (and in some implementations the WAECP) application can mitigate the typically difficult, inefficient, and time consuming process of comparing and validating available GWA water analysis data using particular technical skill/expertise to numerically interpret water analysis data. Fourth, the G-WAST (and in some implementations, the WAECP) application can also enhance the efficiency of performed actions based on GWA water analysis data that can be derived and/or predicted from rapid and simple measurement of water conductivity. For example, and in general, performed actions can include determination of water breakthrough, determination of water invasion, determination of casing leaks between two petroleum reservoirs, prediction of scale precipitation, monitoring sweep, performing remedial/proactive actions based on GWA water analysis data correlation/predictions, and/or other performed actions. Fifth, a generated graphical correlation relating GWEs to each other based on petroleum-wells/groups of wells, -plants, -fields, and/or -reservoirs can provide data useful for, among other things, monitoring and adjusting development of specific petroleum-wells/groups of wells, -plants, -fields, and/or -reservoirs. For example, the described approach for correlating/relating, displaying, and predicting data pertaining to GWEs can be used by one or more elements of an organization (e.g., a petroleum organization can include, among other elements, petroleum engineering, hydrology, producing, and/or reservoir management) to develop different actions particular to their assigned function for the organization. Other advantages will be apparent to those of ordinary skill in the art.

The details of one or more implementations of the subject matter of this specification are set forth in the accompanying drawings and the description below. Other features, aspects, and advantages of the subject matter will become apparent from the description, the drawings, and the claims.

DESCRIPTION OF DRAWINGS

FIG. 2 illustrates a screenshot of a data display presenting a traditionally presented geochemical water analysis (GWA) water analysis data report based on stored GWA water analysis data according to an implementation.

FIGS. 4J-4N illustrate scatterplots based on described user interface options according to an implementation.

Like reference numbers and designations in the various drawings indicate like elements.

DETAILED DESCRIPTION

Figure 1:
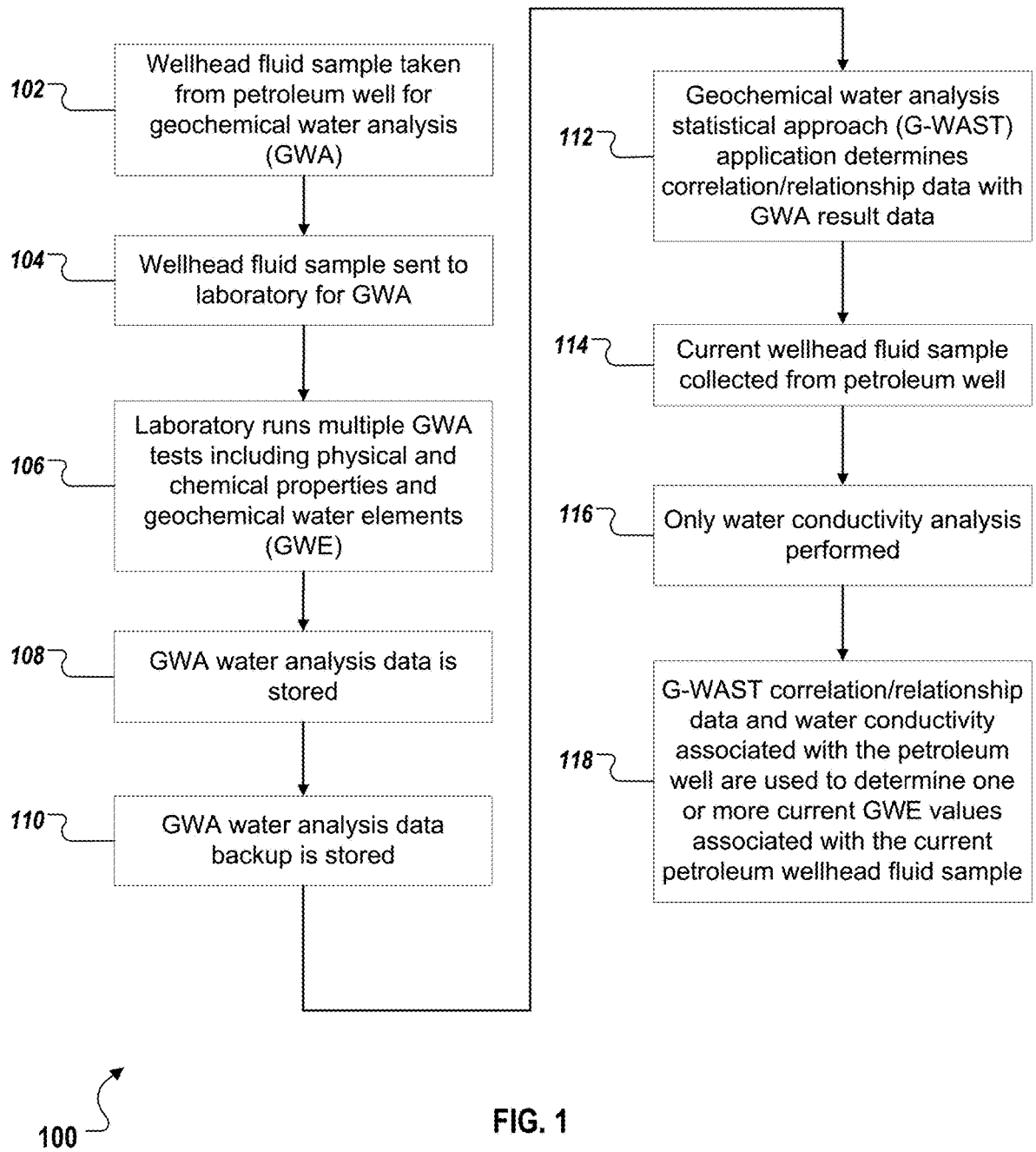
FIG. 1 is a flow chart of a method for correlating and predicting geochemical water elements (GWEs) in a water sample obtained from a petroleum well according to an implementation.

The following description is presented to enable any person skilled in the art to make and use the disclosed subject matter, and is provided in the context of one or more particular implementations. Various modifications to the disclosed implementations will be readily apparent to those skilled in the art, and the general principles defined herein may be applied to other implementations and applications without departing from scope of the disclosure. Thus, the present disclosure is not intended to be limited to the described and/or illustrated implementations, but is to be accorded the widest scope consistent with the principles and features disclosed herein.

Geochemical water analysis (GWA) is a process used to derive water analysis data (e.g., physical and chemical properties) from water samples obtained from petroleum-producing wells. For example, one objective of the GWA is to measure TDS which enables identification of the source of water being analyzed. GWA is typically expensive and requires multiple pieces of expensive lab equipment, technical expertise, and/or measurements of geochemical water element (GWE) concentrations (e.g., pH, water specific gravity, conductivity, sodium (Na), calcium (Ca), magnesium (Mg), chloride (Cl), sulfate, carbonate, bicarbonate, and/or total dissolved solids (TDSs)) of a particular water sample that make up the GWA water analysis data. For example, a lab scientist traditionally has to measure the concentrations of the many GWEs. In some cases, each water sample can require a day or more to fully analyze before a TDS GWE value can be determined. The GWA water analysis data is then typically used for various purposes, including determining water breakthrough, casing leaks between different reservoirs, predicting precipitation of scale, monitoring sweep, water invasion, remedial actions, and/or other purposes. Changes over time in the GWE concentrations in water samples from one or more petroleum-producing wells can provide data useful to determine a reduction or expansion/further development of a petroleum field associated with a petroleum reservoir. The normal practice for comparing and validating available water analysis data is to leverage technical skill/expertise to numerically interpret water analysis data—a difficult, inefficient, and time consuming process that does not leverage correlations and/or relationships that can be efficiently derived from available water analysis data and rapid/simple measurement of water conductivity. It is important to have an efficient, rapid, and simple ability to derive up-to-date data based on prior GWA water analysis data in order to be able to perform special analysis studies and to determine, for example and among other things, the above-mentioned petroleum resource trends and reduction or expansion/further development of the petroleum field associated with the petroleum reservoir.

At a high level, this disclosure generally describes methods and systems, including computer-implemented methods, computer program products, and computer systems, for predicting GWEs in a water sample obtained from petroleum well. Particularly, it is typically desirable to determine total-dissolved solids (TDSs) GWE. At a lower level, the predictions are based on known/established correlations and/or relationships between geochemical water elements associated with existing (e.g., previously gathered/stagnant) GWA water analysis data (e.g., from a particular petroleum well) and a water conductivity value from a current water sample (e.g., associated with the particular petroleum well). In particular, a "geochemical water analysis statistical approach" ("G-WAST") application is used to determine correlations and/or relationships between the GWEs associated with the existing GWA water analysis data and then graphically displaying the determined correlation and/or relationship results using a graphical technique associated with the G-WAST application. In some implementations, a "water analysis elements concentration predication" ("WAECP") application can then be used which provides functionality to automatically predict GWEs (including TDSs) using the G-WAST-determined (established) correlations and/or relationships between the GWEs and a water conductivity data value associated with a current water sample (e.g., from the above-mentioned petroleum well) (including, in some instances, water conductivity data that can be gathered "on-the-fly" from a petroleum well using specialized equipment to gather and analyze a water sample to determine a water conductivity value associated with the water sample). In typical implementations, it is assumed that GWA water analysis data already exists and is available for use to allow rapid analysis and application of resultant correlation/relationship data and GWE predictive determination. In some implementations, the GWA water analysis data can be determined relatively close to an application of the G-WAST (and in some implementations the WAECP) application, but with resultant performance degradation as will be understood by those of ordinary skill in the art.

The data provided by the G-WAST (and in some implementations the WAECP) application can be used to a greater advantage in the development of remedial actions through rapid and simple measurement of water conductivity. A generated graphical correlation relating water analysis elements to each other based on petroleum-wells/groups of wells, -plants, -fields, and/or -reservoirs can provide data useful for, among other things, monitoring and adjusting development of specific petroleum-wells/groups of wells, -plants, -fields, and/or -reservoirs. For example, the described approach for correlating/relating, displaying, and predicting data pertaining to GWEs can be used by one or more elements of an organization (e.g., a petroleum organization can include, among other elements, petroleum engineering, hydrology, producing, and/or reservoir management) to develop different actions particular to their assigned function for the organization.

In the following description and figures, data is illustrated plotted against a Cartesian scale to simplify the example plots for understanding. For example, in typical implementations, if a logarithmic function is active (e.g., as described below—selecting a log scale checkbox to use logarithmic values) for a parameter (e.g., Cl, Na, etc.), logarithmic values for the parameter are not plotted on a logarithmic scale, but are plotted on a Cartesian scale. In other implementations, data can be plotted on any type of scale consistent with the disclosure (e.g., a logarithmic or other type of scale). The use of a Cartesian scale in this disclosure is not meant to limit the disclosure in any way.

FIG. 1 is a flow chart of a method 100 for correlating and predicting GWEs in a water sample obtained from a petroleum well according to an implementation. For clarity of presentation, the description that follows generally describes method 100 in the context of the remaining figures. However, it will be understood that method 100 may be performed, for example, by any other suitable system, environment, software, and hardware, or a combination of systems, environments, software, and hardware as appropriate. In some implementations, various steps of method 100 can be run in parallel, in combination, in loops, or in any order.

At 102, a wellhead fluid sample is collected from petroleum well for geochemical water analysis (GWA). From 102, method 100 proceeds to 104.

At 104, the wellhead fluid sample is sent to a laboratory for GWA analysis. In some implementations, the laboratory is chosen based on particular analysis capabilities, analysis speed, and the like. From 104, method 100 proceeds to 106.

At 106, the laboratory runs multiple tests on the wellhead fluid sample as part of GWA. The tests can determine physical and chemical properties of the wellhead fluid sample that include physical properties and geochemical water element (GWE) concentrations (collectively GWA parameters) to generate GWA water analysis data. In typical implementations, GWA water analysis data can include, for example, pH, water specific gravity, conductivity, sodium (Na), calcium (Ca), magnesium (Mg), chloride (Cl), sulfate, carbonate, bicarbonate, total dissolved solids (TDSs), and/or other elements. From 106, method 100 proceeds to 108.

At 108, the determined GWA water analysis data is stored for use. For example, in some implementations, the GWA water analysis data is stored into a persistent memory storage such as a database of any suitable type. From 108, method 100 proceeds to 110.

At 110, the determined GWA water analysis data is stored as a backup in any suitable persistent memory storage, such as a database. For example, in some implementations, the backup data can be stored in an offsite data repository, in a separate local and/or remote database, or within the same database used in 108. From 110, method 100 proceeds to 112.

At 112, "geochemical water analysis statistical approach" ("G-WAST") application is used to determine correlations and/or relationships between the GWA parameters (e.g., physical properties such as pH, water specific gravity, conductivity, and GWEs such as sodium (Na), calcium (Ca), magnesium (Mg), chloride (Cl), and/or total dissolved solids (TDS)) associated with the existing GWA water analysis data and then graphically display the determined correlation and/or relationship results using a graphical technique associated with the G-WAST application.

Turing now to FIG. 2, FIG. 2 illustrates a screenshot 200 of a data display presenting a traditionally presented GWA water analysis data report 202 (e.g., as a numerical-type table 204). In some implementations, for example, report output format can be selected to be XL S, XLSX, RTF, PDF, and/or other output format based on GWA water analysis data as stored in 108 and 110 according to an implementation. In this format, the GWA water analysis data requires specialized training and skill to interpret and use/apply for the various above-described purposes.

Figures 3A, 3B:
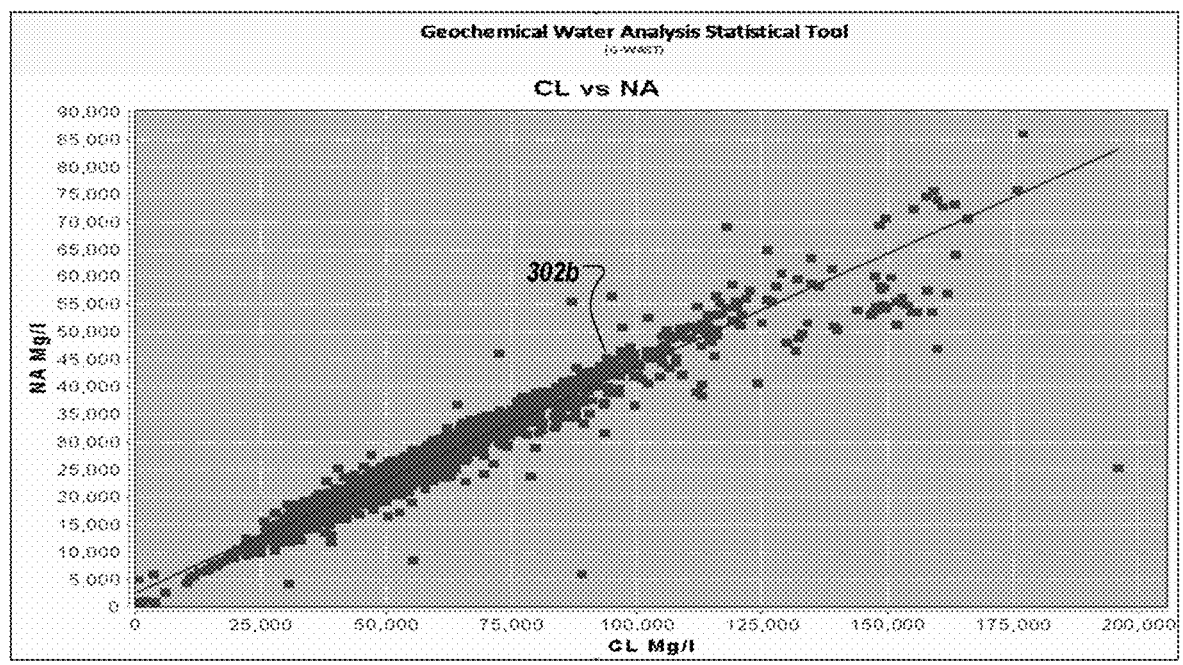
FIGS. 3A-3D illustrate screenshots of data displays illustrating the difference between traditionally presented GWA water analysis data report data (similar to that of FIG. 2) in FIGS. 3A & 3C and correlated/related data as presented by a "geochemical water analysis statistical approach" ("G-WAST") application in FIGS. 3B and 3D, respectively, according to an implementation.
Figures 3C, 3D:
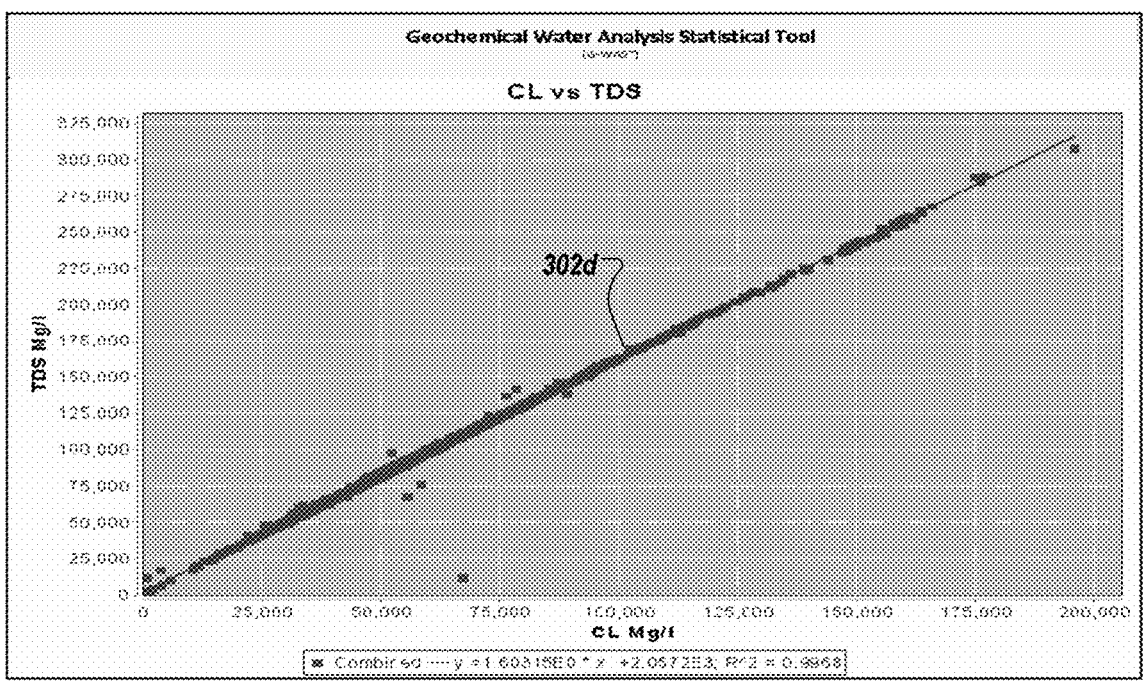

Turning now to FIGS. 3A-3D, FIGS. 3A-3D illustrate screenshots 300a-300d of data displays illustrating the difference between traditionally presented GWA water analysis data report data (similar to that of FIG. 2) in FIGS. 3A & 3C and correlated/related data as presented by the G-WAST application in FIGS. 3B and 3D, respectively, according to an implementation.

For example, data displayed in screenshot 300a of FIG. 3A, can be used to generate a correlation/relationship between amounts of chloride (Cl) and sodium (Na) in a water sample, but the presented numerical table 302a does not present an easily discernable correlation/relationship between the chloride (Cl) and sodium (Na) data values. Turning to FIG. 3B, a screenshot 300b of a G-WAST-generated report graphically displays a scatterplot 302b of a determined correlation between chloride (Cl) and sodium (Na) data values allowing a rapid, visual analysis of the presented data.

Similarly, data displayed in screenshot 300c of FIG. 3C, can be used to generate a correlation/relationship between amounts of chloride (Cl) and TDSs in a water sample, but the presented numerical table 302c does not present an easily discernable correlation/relationship between the Cl and TDS data values. Turning to FIG. 3D, the generated G-WAST report screenshot 300d graphically displays a scatterplot of a determined correlation between Cl and TDS data values allowing a rapid, visual analysis of the presented data. The G-WAST reports can be used to generate a dynamic correlation/relationship between GWA parameters that can be used to develop a group of correlations and customized different correlations among GWA water analysis data.

In typical implementations, the G-WAST, WAECP, and/or other applications executed as part of correlating and predicting GWEs in a water sample obtained from a petroleum well are built using the JAVA programming language. In other implementations, as will be understood by those of ordinary skill in the art, other programming languages, in whole or in part, can be used to develop the described applications with equivalent functionally. The use of any suitable programming language is considered to be within the scope of this disclosure.

GWA water analysis data is retrieved (e.g., using ORACLE's PL/SQL and/or other suitable database query language) from the above-described database (e.g., an ORACLE database) to be processed by the G-WAST application. Processing includes operations such as calculating a reacting value and a percentage reacting value for GWAEs using predefined formulas according to element concentration (e.g., in mg/l), molecular weight, and valence. An on-the-fly calculation can be made for each element in the G-WAST application. A reacting value equal element concentration in mg/l is divided by the equivalent weight for each element. The equivalent weight for each element is equal to the molecular weight of the element divided by the valence for each element. Output of the G-WAST application is typically in an EXCEL or PDF format, but other formats are possible and considered to be within the scope of this disclosure.

Figure 4A:
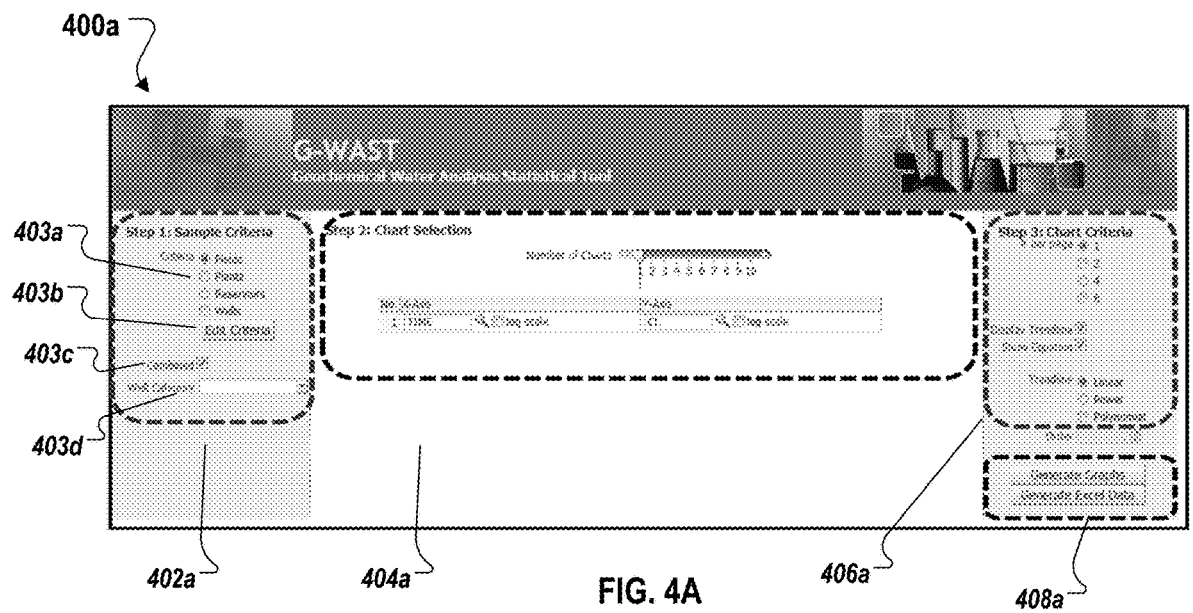
FIGS. 4A-4F are screenshots of functionality provided by the G-WAST application through various user interfaces according to an implementation.

FIGS. 4A-4F are screenshots 400a-400f of functionality provided by the G-WAST application through various user interfaces according to an implementation. FIG. 4A illustrates typical G-WAST application functionality to select data sample criteria 402a, select chart selection criteria 404a, select chart criteria 406a, and a selection for output type 408a. As illustrated, data sample criteria 402a includes selections 403a for fields, plants, reservoirs, and/or wells. A selection of a particular criterion will include data related to that criterion to be displayed. In typical implementations, an "edit criteria" button 403b is included as part of the selection of data sample criteria 402a and allows addition, removal, and/or modification of presented selectable criteria values.

In typical implementations, the functionality to select data sample criteria 402a includes a combined checkbox 403c and a well category selection menu 403d. The combined checkbox 403c typically allows multiple selected criteria to be considered together for illustration and subsequent calculations if desired. The well category selection menu 403d typically presents well categories for selection such as "oil producer," "oil standing producer," "observation," "abandoned," or other well category.

Figure 4B:
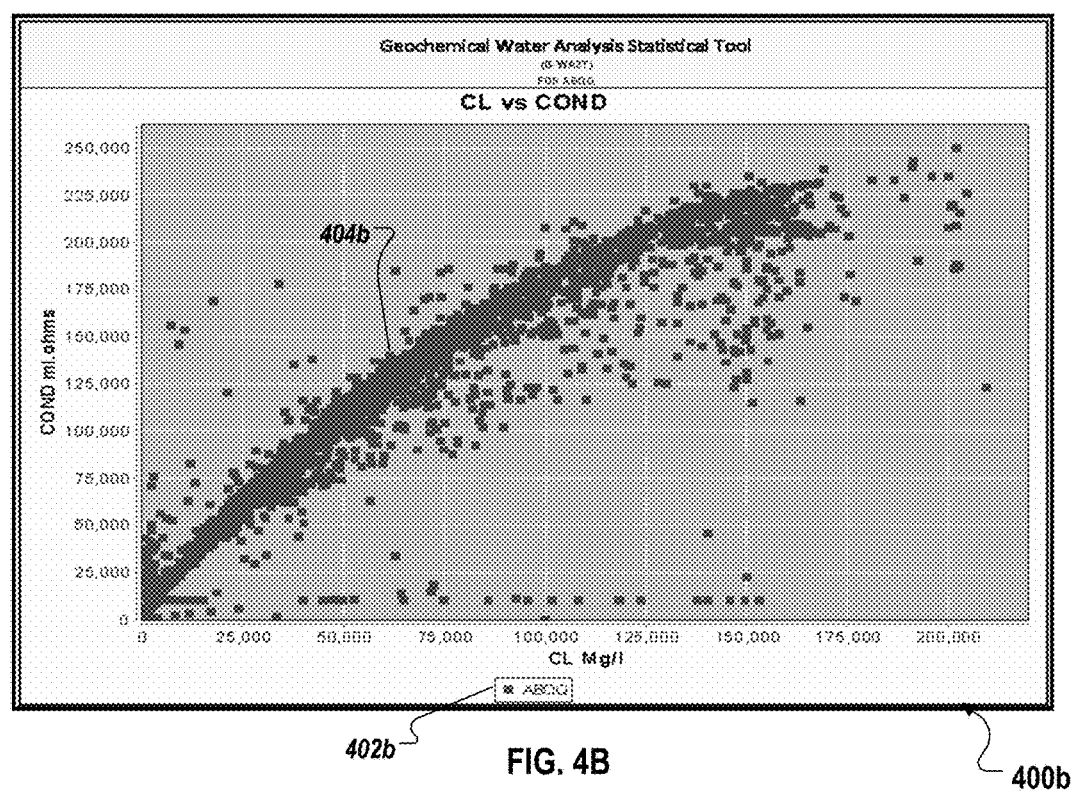

Turning to FIG. 4B, FIG. 4B illustrates a screenshot 400b of a scatterplot based on a selected sample criteria 402a of "Fields" with multiple selected criteria considered together (i.e., the combined checkbox is selected). In the illustrated example, the field "ABQQ" 402b has been selected and data related to this field is plotted in the displayed scatterplot "CL VS COND."

Figure 4C:
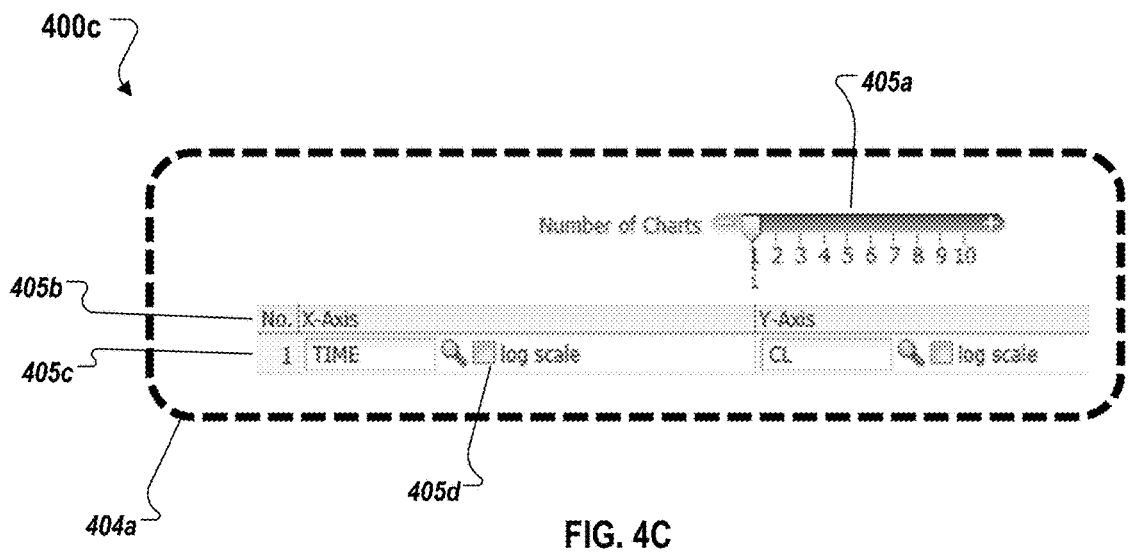
Figure 4D:
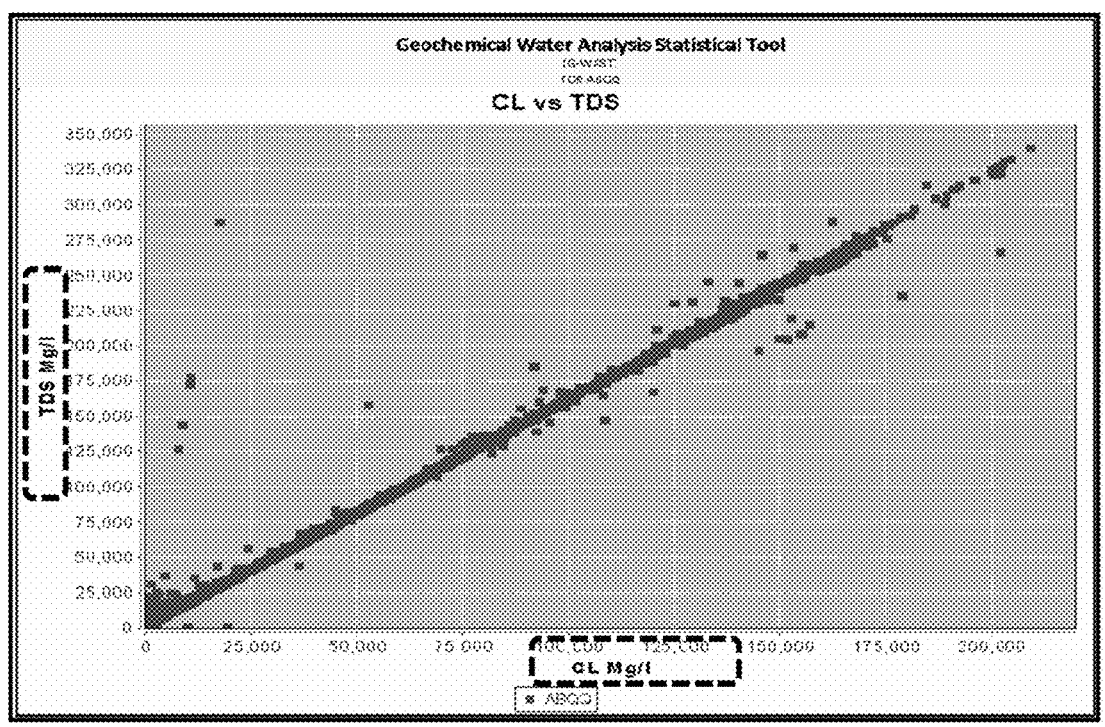
Figure 4E:
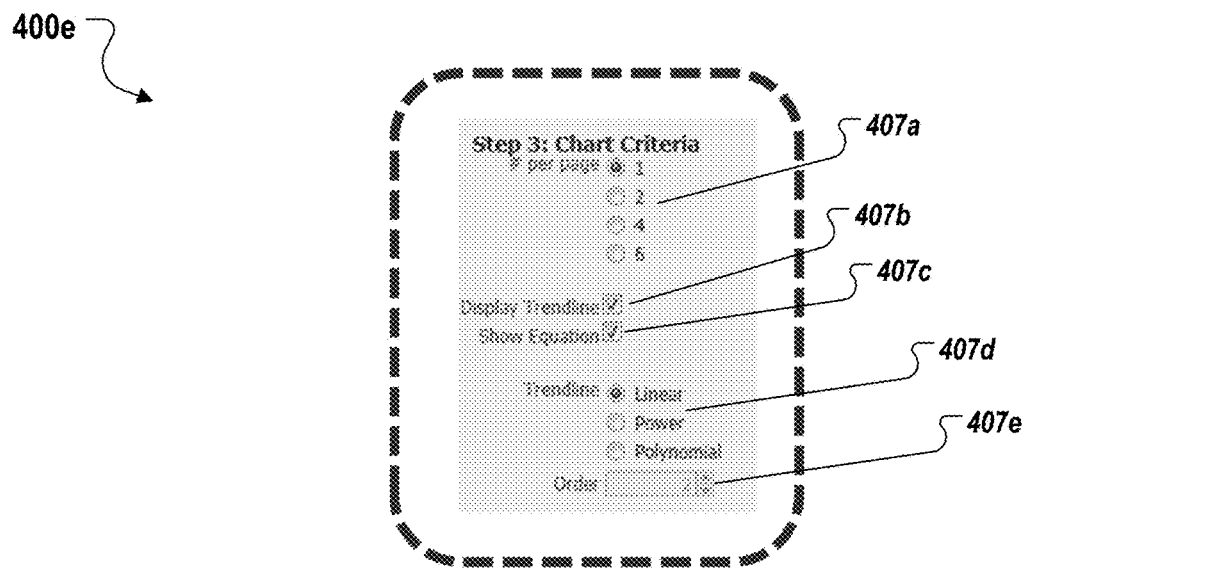
Figure 4F:
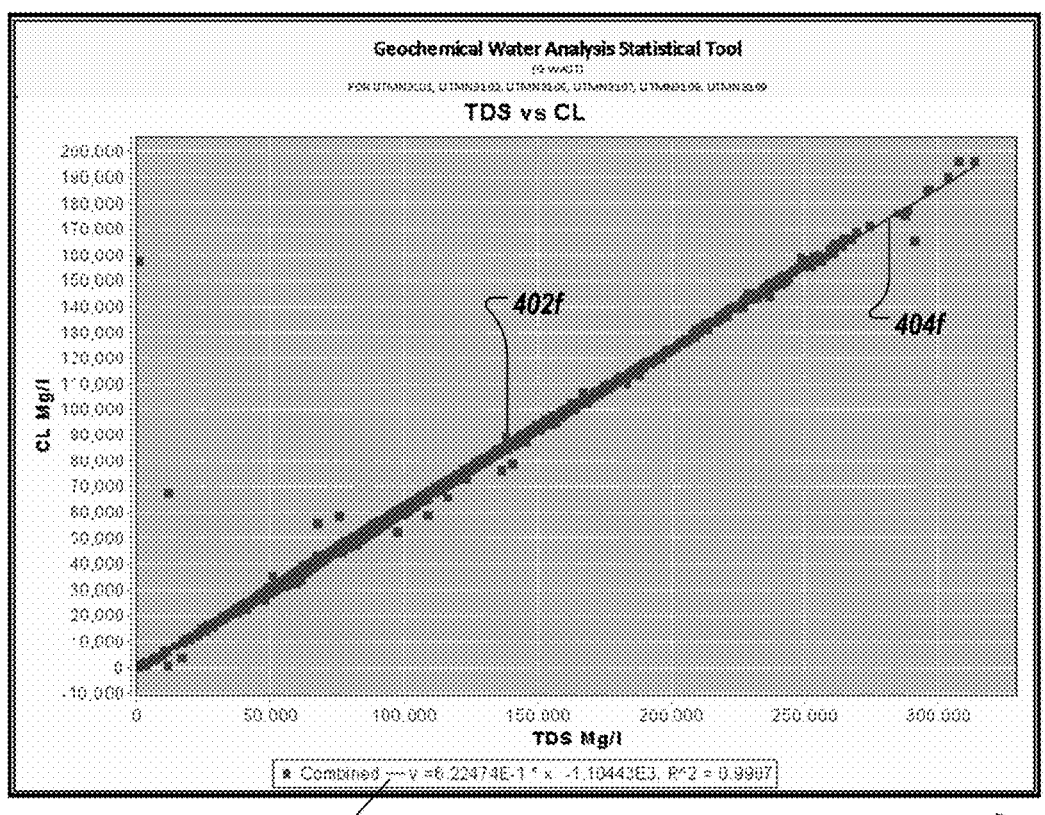
Figure 4G:
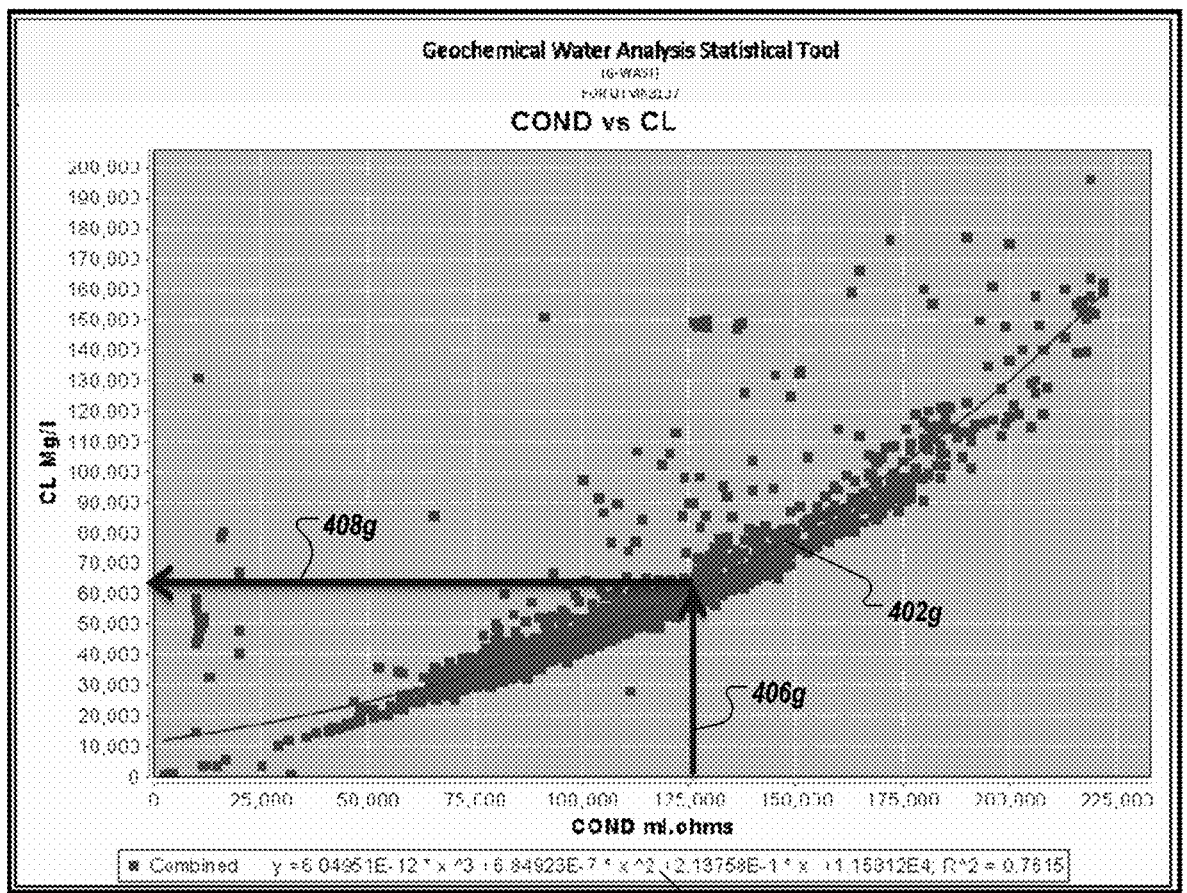
FIG. 4G is a screenshot of a G-WAST-generated scatterplot illustrating determination of a new GWE value based on a newly determined water conductivity value according to an implementation.
Figure 4H:
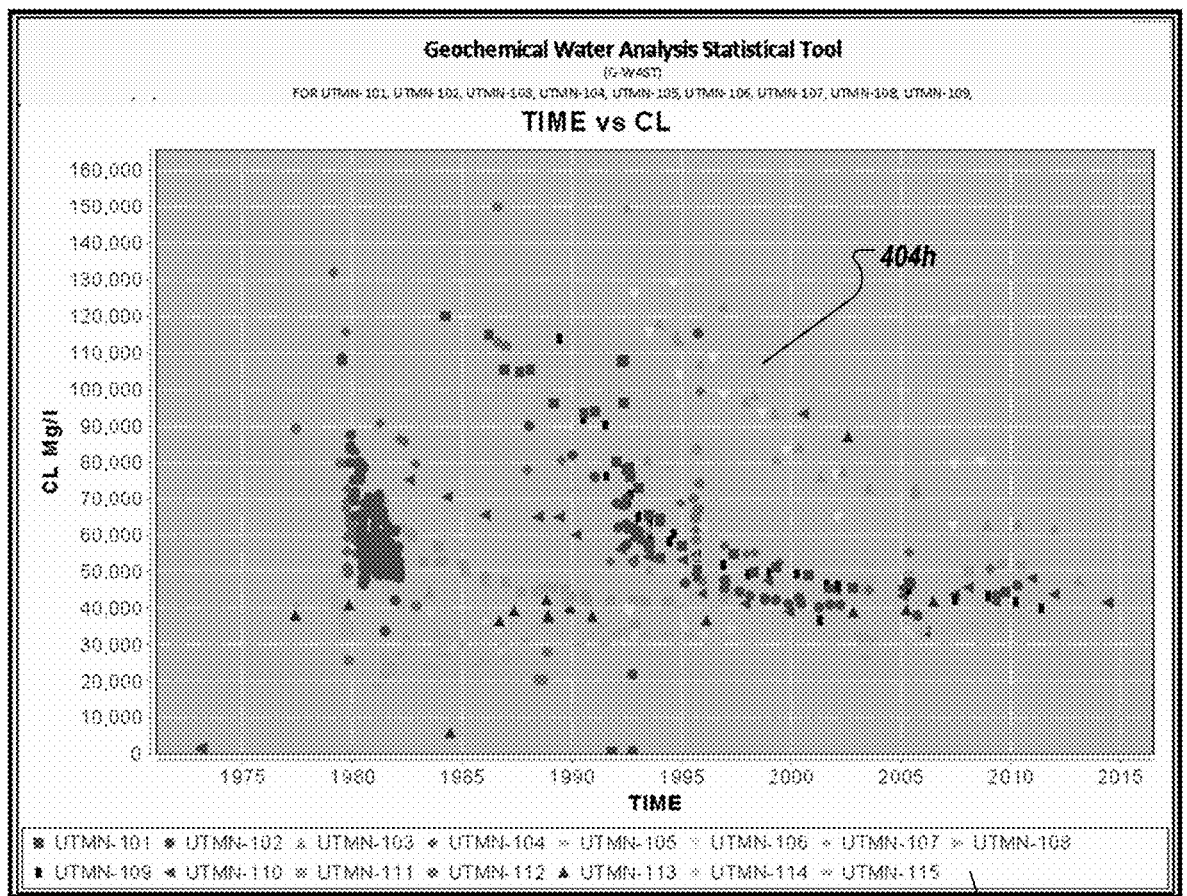
FIG. 4H illustrates an example scatterplot where the combined checkbox is not selected for a group of wells with the X-Axis having a "Time" value selected and the Y-Axis having a chloride "CL" value selected according to an implementation.

As an alternative example, FIG. 4H illustrates an example scatterplot 400h where the combined checkbox 403c is not selected for a group of wells with the X-Axis having a "Time" value selected and the Y-Axis having a chloride "CL" value selected according to an implementation. In typical cases, when the combine checkbox 403c is not selected, a maximum of a predefined number of data points per criteria will be displayed. For example, in FIG. 4H, criteria 402h are displayed as separate data points 404h on the TIME vs CL scatterplot 400h. Note that, for example, the illustrated data points of wells UTMN-101 are represented in FIG. 4H as dark gray squares and data points of well UTMN-111 are represented by lighter gray squares. In some implementations, these or other illustrated data points can be represented by differing colors (for example, red, blue, green, yellow, pink, and the like). Note that for FIG. 4H, a show equation checkbox 407c (see below) is not selected.

Figure 4I:
FIG. 4I is a screenshot of a number of charts selection set equal to '4' according to an implementation.

Turning to FIG. 4C, FIG. 4C represents the chart selection criteria 404a identified in screenshot 400a of FIG. 4A. The chart selection criteria 404a presents a number of charts selection 405a allowing a selection of a number of charts (e.g., one through ten in the illustrated example) to generate with the selected data and criteria. Axis selection criteria 405b are made available (e.g., X-Axis and Y-Axis) as well as axis data entry fields 405c for each chart. In the provided example, only one chart is selected in the number of charts selection 405a. If, for example, four charts were selected, additional data entry lines with corresponding data entry fields 405c for each axis per chart would be presented (e.g., one line for each chart for a total of four—refer to FIG. 4I for an example graphical user interface implementation where a number of charts='4' 402i has been selected). The data entry fields 405c are used to select a particular data type that will be plotted on a particular axis. For example, in the illustrated example, the X-Axis has a "Time" value selected and the Y-Axis has a chloride "CL" value selected. Additionally, a log scale checkbox 405d is presented for each data entry field 405c. In typical implementations, the scale is Cartesian (log scale checkbox 405d not selected) or logarithmic values for water analysis parameters on a Cartesian scale (log scale checkbox 405d selected). Note that the log scale checkbox 405d is independently selectable for each axis. Note also that screenshot 400b of FIG. 4B is an example of a scatterplot generated for one field (ABQQ) with Cartesian scale values of an X-Axis value of chloride "CL" and a Y-Axis value of Conductivity "COND." Turning to FIG. 4D, FIG. 4D is a screenshot 400d of an example of a scatterplot generated with Cartesian scale values of an X-Axis value of "CL" and a Y-Axis value of Total Dissolved Solid "TDS" for one field (ABQQ) on Cartesian scale.

Turning to FIG. 4E, FIG. 4E represents the select chart criteria 406a identified in screenshot 400a of FIG. 4A. The select chart criteria 406a presents a number of charts per page selection 407a allowing a selection of a number of charts per displayed page (e.g., 1, 2, or 4 charts displayed on a single page), a display trendline checkbox 407b, the show equation checkbox 407c mentioned above, a trendline type selection 407d (e.g., linear, power, or polynomial with orders), and an order entry field 407e (if the selected trendline type selection 407d is of type "polynomial").

Turning to FIG. 4F, FIG. 4F is a screenshot 400f of a scatterplot 402f, a displayed trendline 404f, an associated dynamic equation 406f. As illustrated, a user can display the trendline 404f and associated dynamic equation 406f The user can manipulate the trendline 404f degree and type until the trendline 404f fits the plotted data points. For example, the user would want to adjust the trendline 404f until the angle was within and conformed (i.e., "fit") the plotted data points of the scatterplot 402f In typical implementations, the dynamic equation 406f is not directly changeable by a user. The trendline degree can be changed manually using the trendline type selection 407d and through the use of a polynomial order if the trendline is a polynomial. The dynamic equation 406f is generated based on the chart data that depends on GWA water analysis data and the processed data in some parameters, such as reacting value, percentage reacting value, and logarithmic function for any selected GWA parameters. The dynamic correlation coefficient in equation 406f is based on the axis data entry fields 405c selection for each chart for GWA water analysis parameters (e.g., two data points) and a correlation matrix.

For example, in some implementations, the correlation factor can be obtained using a formula similar to:

```
// GETTING THE CORRELATION FACTOR R^2
Number[ ][ ] xyNumberArray = new Double[2][ ];
for (int j = 0; j < dataCorrelation.length; j++)
{
    xyNumberArray[j] = new Double[dataCorrelation[j].length];
    for (int k = 0; k < dataCorrelation[j].length; k++)
    {
        xyNumberArray[j][k] = dataCorrelation[j][k];
        System.out.println("("+j+","+k+") "+dataCorrelation[j][k]);
    }
}
```

The result is a matrix, for example (only a few values illustrated):
  (0,0) 2.26098E11
  (0,1) 2.33874E11
  (0,2) 2.616084E11
  (0,3) 2.62818E11
  (0,4) 2.640276E11
  (0,5) 2.647188E11
  (0,6) 2.652372E11
  (0,7) 2.65842E11 . . . .
In some implementations, the result can be used in the following manner:
  double correlationFactor=
  Statistics.getCorrelation(xyNumberArray[0], xyNumberArray[1]);
  System.out.print ln("correlationFactor="+correlationFactor);
  (0,1) 2.33874E11
  correlationFactor=0.1787790521824116 equation.append("; R^2="+
  correlationFormatter.format(Math.pow(correlationFactor, 2)));
  System.out.print ln("Math.pow(correlationFactor, \n"+ 2)="+
  Math.pow(correlationFactor, 2));
  Math.pow(correlationFactor, 2)=0.03196194949924145.

In typical implementations, the data is plotted on the graph by a JAVA library JFREECHART. To generate any graph, example steps to be followed, for example, include: select sample criteria 403a (field, plants, reservoir, and/or wells), choose the selected criteria using "edit criteria" button 403b (e.g., field such as field-A, field-B, field-c, . . . , etc. or plants such as plant-1, plant-2, plant-3, etc., or reservoir and/or formations such as reservoir/formation-1, reservoir/formation-2, reservoir/formation-3, etc., or wells such as well-100, well-200, well-300, etc.), if looking to compile one of the previous selections such as three fields (field-A, field-B, and field-c) to generate one correlation and/or one relationship for the three fields; the checkbox 403c to be considered together the correlation and/or one relationship. Following these selections, select well category 403d (e.g., oil producer, oil standing producer, observation, etc.) for the previous selected sample criteria. Next, select a number of charts 405a, for example, four charts; next, select the four relations for the previous selected sample criteria which need to be displayed through axis selection criteria 405b, for example, Cl vs Conductivity, Na vs Cl, Cl vs TDS, etc. If log values are required for X-Axis and Y-Axis, a log scale checkbox 405d is presented for each data entry field 405c. Next, select chart criteria 406a to present a number of charts per page (e.g., 1, 2, or 4 charts displayed on a single page). Next, the user can select check boxes to display a trendline (checkbox 407b) and to show an equation (checkbox 407c). A trendline-type selection 407d (e.g., linear, power, or polynomial with orders) can be selected; otherwise, the user can manipulate the trendline after generating graphs using the "generate graphs button" 408a. Generating dynamic equations and/or relationships can be made through sample criteria selection 402a for different fields, plants reservoir, and wells. In other implementations, other plotting/graphing software, commercial and/or proprietary, can provide the described graphing functionality.

Referring back to FIG. 4A, selection for output type 408a allows generation of graphs (e.g., as displayed in FIGS. 3D, 3B, 4B, 4D, 4F, etc.) or EXCEL data (e.g., as displayed in FIGS. 3B and 3D) as desired. In some implementations, both display formats can be selected to be generated simultaneously (e.g., displaying each on a page for comparison, etc.). In other implementations, other output formats can also be generated as will be understood by those of ordinary skill in the art. Output formats consistent with this disclosure are also considered be within the scope of the disclosure.

Figure 4J:
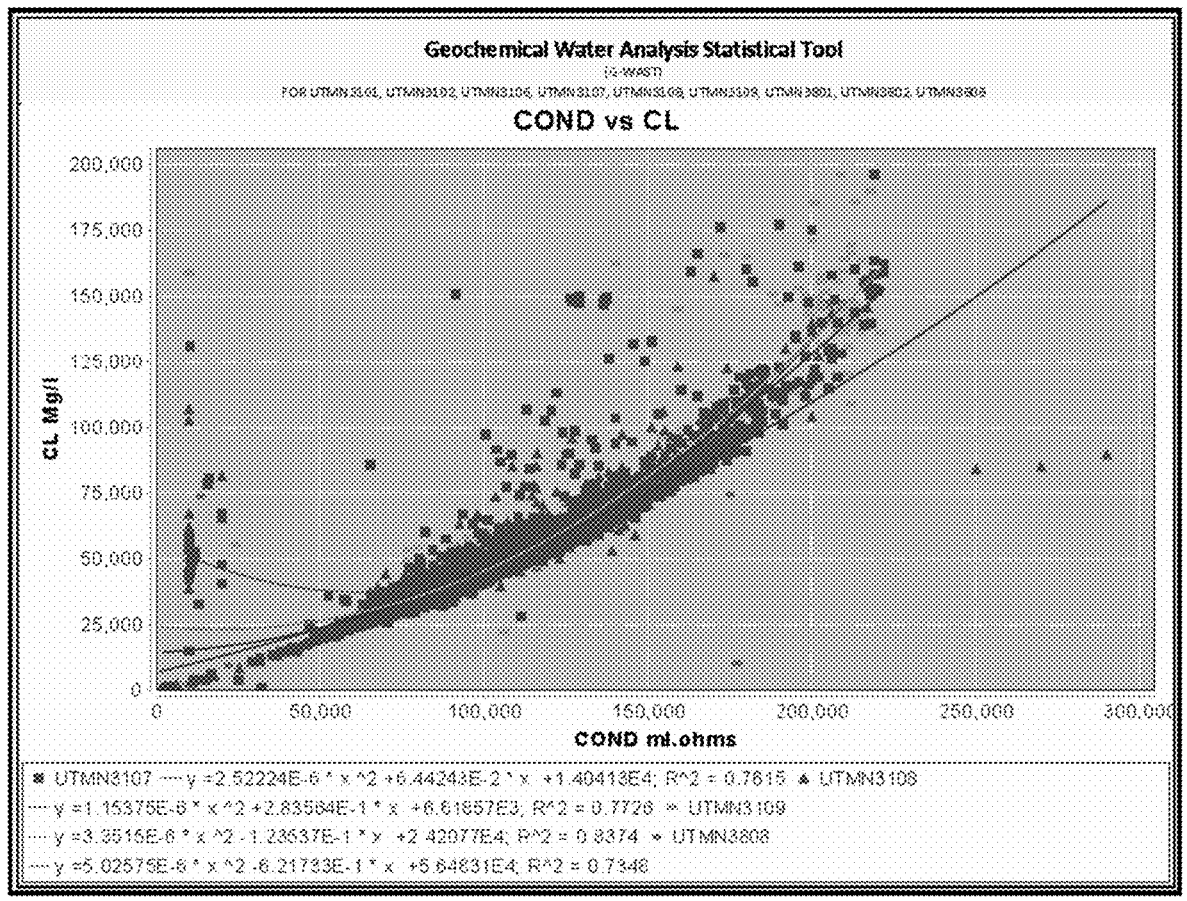
Figure 4K:
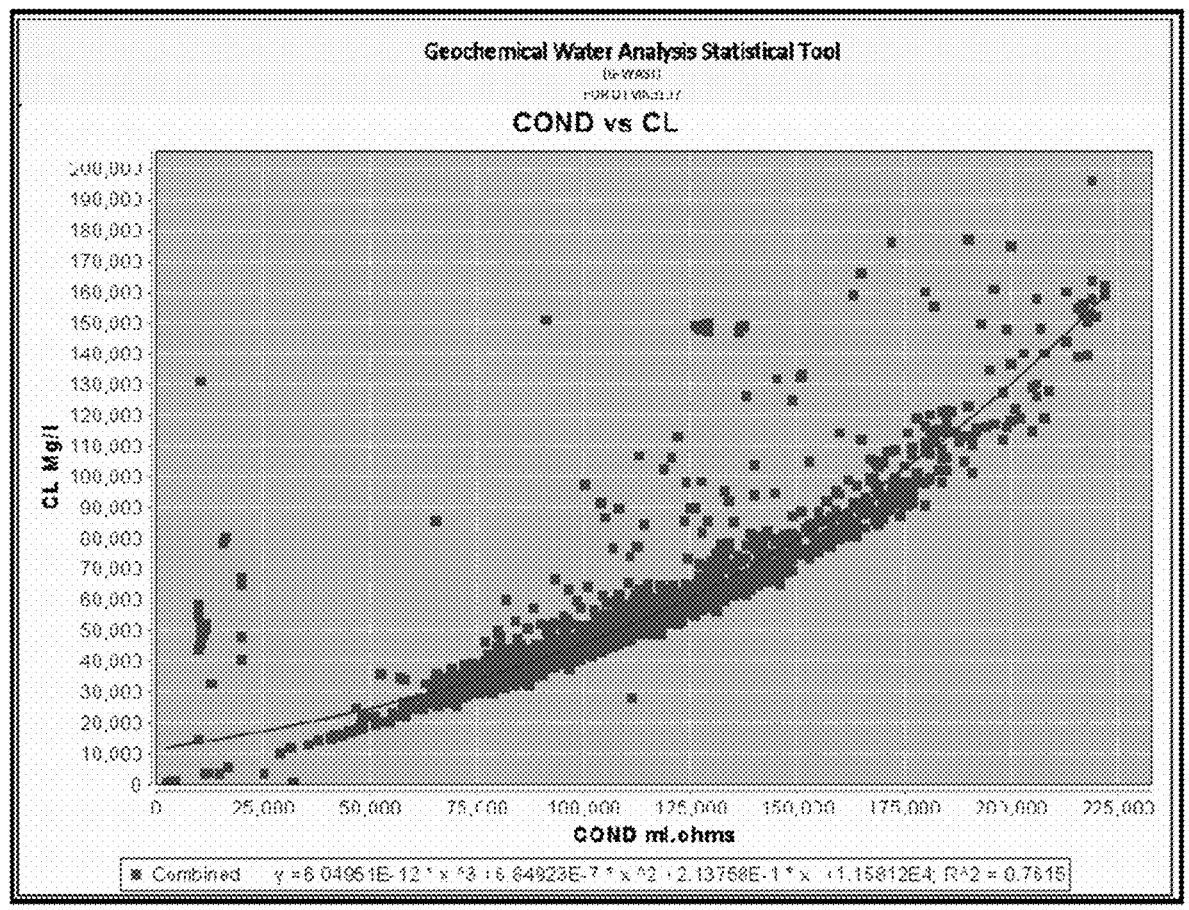
Figure 4M:
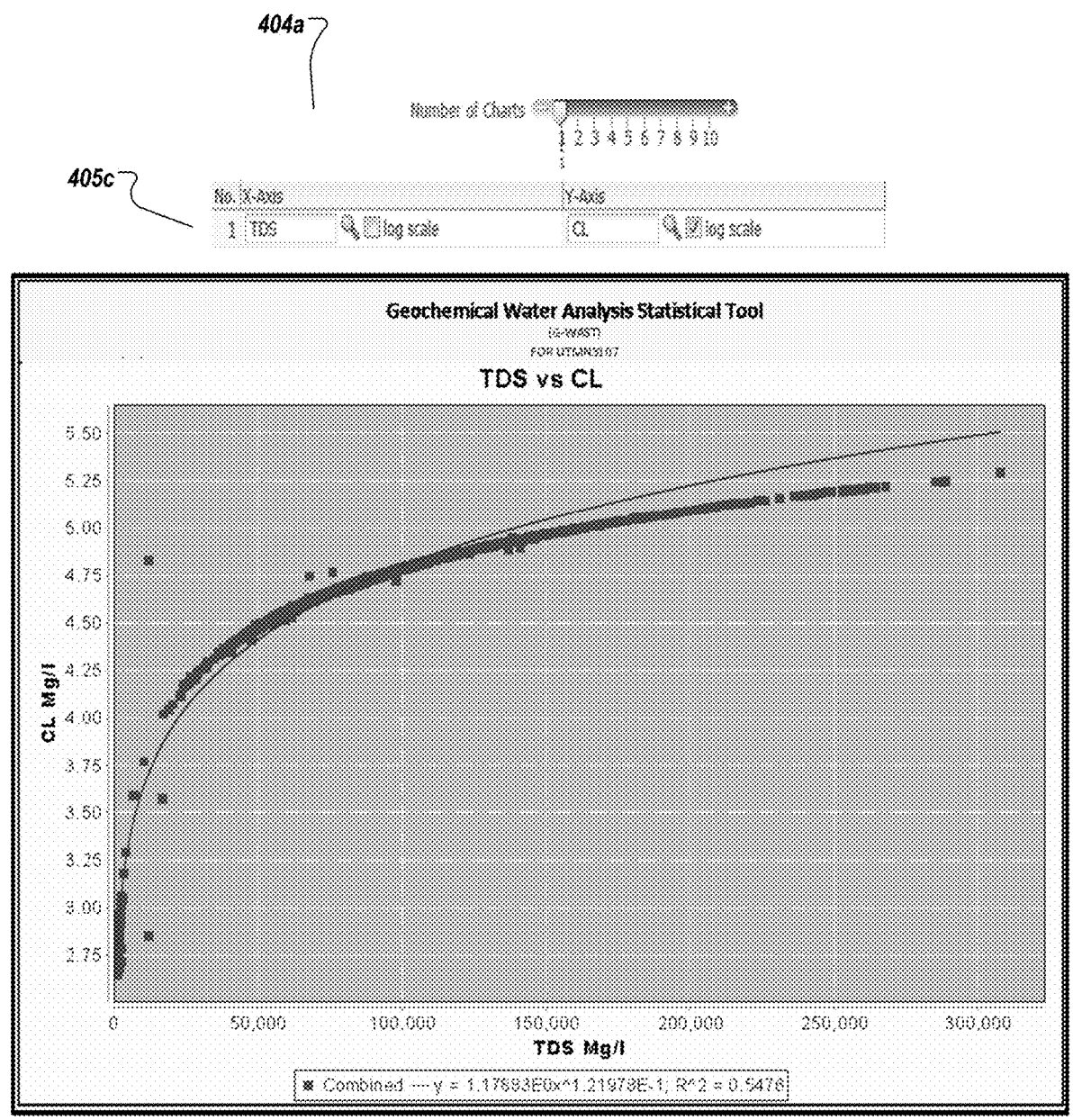
Figure 4N:
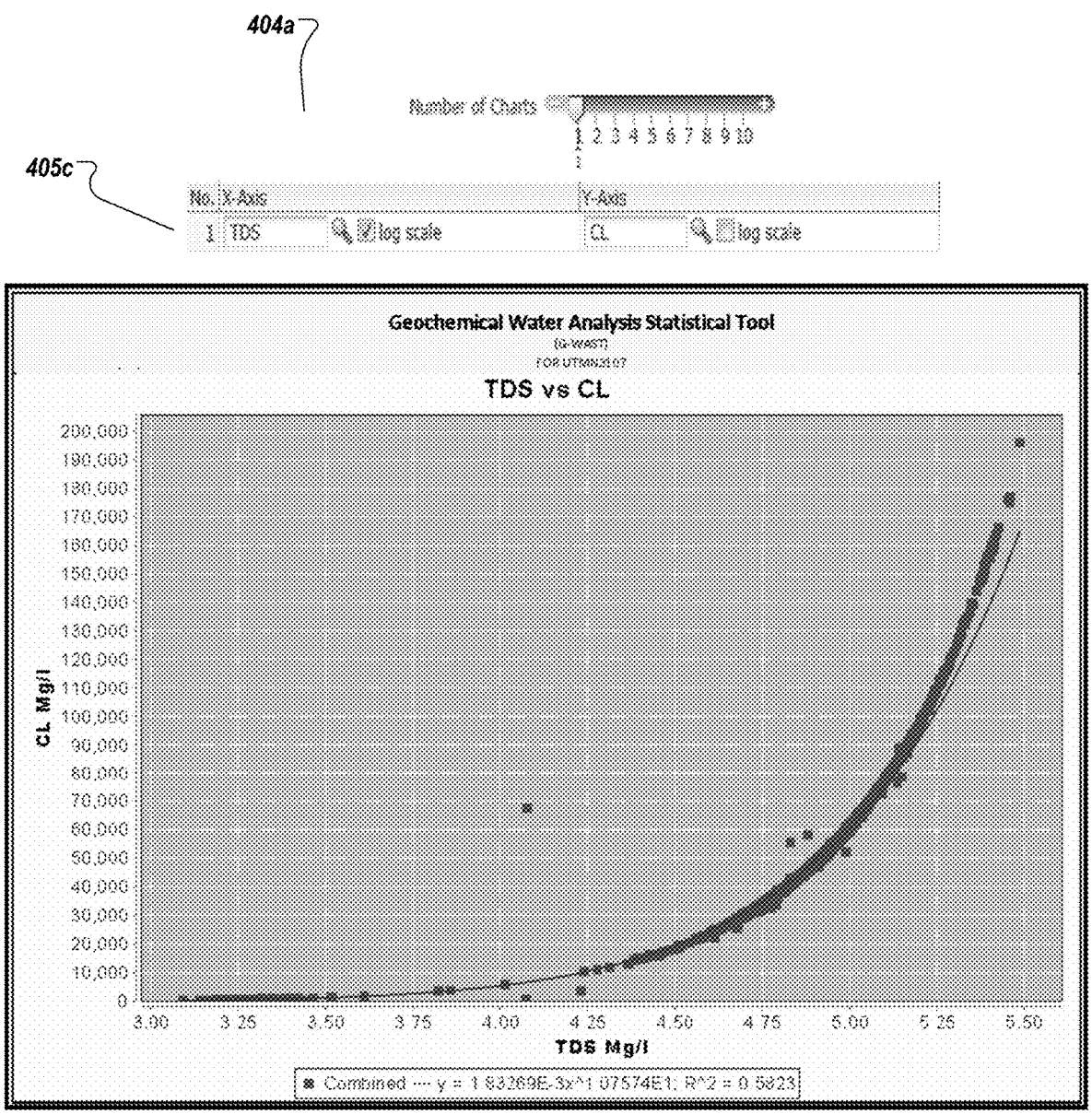

In the case of a selected output type 408a of graph, applicable GWA water analysis data is analyzed, correlated, etc. and output data is plotted on a scatterplot (e.g., GWA water analysis data points and calculated data for reacting value and a percentage reacting value based on predefined formulas) according to selections made using, for example, the user interface described in FIGS. 4A-4N. In typical implementations, the displayed graph type is a scatterplot, but in other implementations, other types of graphs can be made available consistent with the data and this disclosure. A user also has an option to view applicable generated data in an spreadsheet-type environment (e.g., an EXCEL spreadsheet) and to analyze/correct/modify source GWA water analysis data if any data outliers exist that negatively impact the G-WAST output data.

FIG. 4J illustrates a scatterplot 400j based on the above-described user interface options according to an implementation. Here, FIG. 4J illustrates non-combined data from a group of wells where different equations and trendlines for data from each particular well are selected to be illustrated. Note that the illustrated data points of well UTMN3107 are represented in FIG. 4J as gray squares and data points of well UTMN3108 are represented by gray triangles. In other implementations, these illustrated data points can be represented by differing colors (for example, red, blue, green, yellow, pink, and the like).

FIG. 4K illustrates a scatterplot 400k based on the above-described user interface options according to an implementation. Here, FIG. 4K illustrates combined data from a group of wells where only one equation and trendline are illustrated.

FIG. 4L illustrates a scatterplot 400l based on the above-described user interface options according to an implementation. Here, FIG. 4L illustrates X- and Y-Axis logarithmic values with the log scale checkbox 405d selected for each axis, but in typical implementations, the data is plotted on a Cartesian scale.

FIG. 4M illustrates a scatterplot 400m based on the above-described user interface options according to an implementation. Here, FIG. 4M illustrates X- and Y-Axis with different log scale checkbox 405d settings. For example, in FIG. 4M, the X-Axis reflects normal TDS values while the Y-Axis reflects logarithmic CL values. In typical implementations, the resulting data is plotted on a Cartesian scale.

FIG. 4N illustrates a scatterplot 400n based on the above-described user interface options according to an implementation. Here, FIG. 4N illustrates X- and Y-Axis with different log scale checkbox 405d settings. For example, in FIG. 4N, the X-Axis reflects logarithmic CL values while the Y-Axis reflects normal TDS values. In typical implementations, the resulting data is plotted on a Cartesian scale.

Returning to FIG. 1, from 112, method 100 proceeds to 114. At 114, a current wellhead fluid sample is collected from a petroleum well. Here, it is desired to calculate one or more GWA values for the current water sample based on the known correlations/relationships associated with the older GWA water analysis data. From 114, method 100 proceeds to 116.

At 116, only a water conductivity analysis is performed on the water sample collected from the petroleum well to determine the water sample's current water conductivity value. From 116, method 100 proceeds to 118.

At 118, the G-WAST correlation/relationship data and the current water conductivity value are used to determine one or more current GWA parameters values associated with the current petroleum well water sample. For example, turning to FIG. 4G, FIG. 4G is a screenshot 400g of a G-WAST-generated scatterplot 402g illustrating determination of a new geochemical water element (GWE) chloride (Cl) value based on a newly determined water conductivity value according to an implementation. Here, FIG. 4G, a correlation scatterplot 402g and dynamic equation 404g determined using older GWA water analysis data between conductivity "COND" and chloride "Cl" for specific sample criteria of a plant concerned with a sample collected from a well located in vicinity of the plant. Once 114 and 116 above have been performed, the dynamic equation 404g is used with the newly determined water conductivity value 406g to determine the current GWE value 408g for Cl for the current water sample. Note that in FIG. 4G, the arrows are for visualization purposes. In some implementations, the arrows or any other indication can be used to assist a user to determine the current GWE value 408g for Cl (or other GWE). After 118, method 100 stops.

Figure 5:
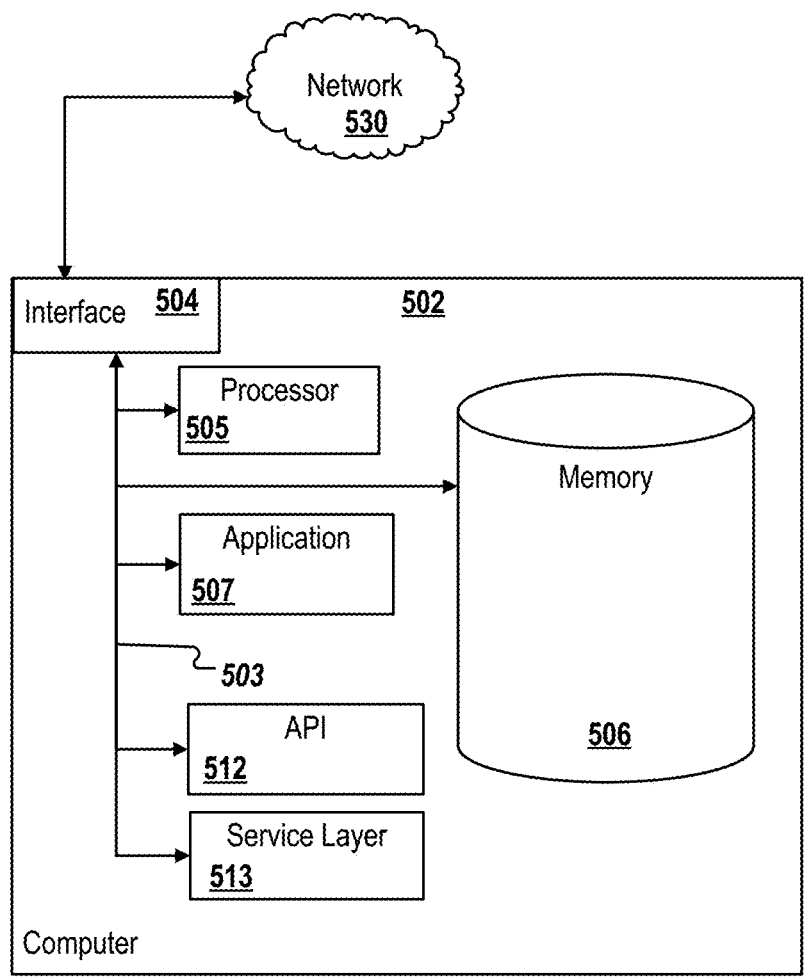
FIG. 5 is a high-level architectural block diagram of a computer system for correlating and predicting GWEs in a water sample obtained from a petroleum well according to an implementation.

FIG. 5 is a block diagram 500 of an exemplary computer 502 used for predicting geochemical water elements GWEs in a water sample according to an implementation. The illustrated computer 502 is intended to encompass any computing device such as a server, desktop computer, laptop/notebook computer, wireless data port, smart phone, personal data assistant (PDA), tablet computing device, one or more processors within these devices, or any other suitable processing device, including both physical and/or virtual instances of the computing device. Additionally, the computer 502 may comprise a computer that includes an input device, such as a keypad, keyboard, touch screen, or other device that can accept user information, and an output device that conveys information associated with the operation of the computer 502, including digital data, visual and/or audio information, or a GUI.

The computer 502 can serve as a client, network component, a server, a database or other persistency, and/or any other component of a computer system for predicting geochemical water elements GWEs in a water sample. The illustrated computer 502 is communicably coupled with a network 530. In some implementations, one or more components of the computer 502 may be configured to operate within a cloud-computing-based, local, global, and/or other environment.

At a high level, the computer 502 is an electronic computing device operable to receive, transmit, process, store, or manage data and information associated with predicting geochemical water elements GWEs in a water sample. According to some implementations, the computer 502 may also include or be communicably coupled with an application server, e-mail server, web server, caching server, streaming data server, business intelligence (BI) server, and/or other server.

The computer 502 can receive requests over network 530 from a client application (e.g., executing on another computer 502) and respond to the received requests by processing the said requests in an appropriate software application. In addition, requests may also be sent to the computer 502 from internal users (e.g., from a command console or by other appropriate access method), external or third parties, other automated applications, as well as any other appropriate entities, individuals, systems, or computers.

Each of the components of the computer 502 can communicate using a system bus 503. In some implementations, any and/or all the components of the computer 502, both hardware and/or software, may interface with each other and/or the interface 504 over the system bus 503 using an application programming interface (API) 512 and/or a service layer 513. The API 512 may include specifications for routines, data structures, and object classes. The API 512 may be either computer language-independent or -dependent and refer to a complete interface, a single function, or even a set of APIs. The service layer 513 provides software services to the computer 502 and/or other components (whether or not illustrated) that are communicably coupled to the computer 502. The functionality of the computer 502 may be accessible for all service consumers using this service layer. Software services, such as those provided by the service layer 513, provide reusable, defined business functionalities through a defined interface. For example, the interface may be software written in JAVA, C++, or other suitable language providing data in extensible markup language (XML) format or other suitable format. While illustrated as an integrated component of the computer 502, alternative implementations may illustrate the API 512 and/or the service layer 513 as stand-alone components in relation to other components of the computer 502 and/or other components (whether or not illustrated) that are communicably coupled to the computer 502. Moreover, any or all parts of the API 512 and/or the service layer 513 may be implemented as child or sub-modules of another software module, enterprise application, or hardware module without departing from the scope of this disclosure.

The computer 502 includes an interface 504. Although illustrated as a single interface 504 in FIG. 5, two or more interfaces 504 may be used according to particular needs, desires, or particular implementations of the computer 502 and/or functionality for predicting geochemical water elements GWEs in a water sample. The interface 504 is used by the computer 502 for communicating with other systems in a distributed environment that are connected to the network 530 (whether illustrated or not). Generally, the interface 504 comprises logic encoded in software and/or hardware in a suitable combination and operable to communicate with the network 530. More specifically, the interface 504 may comprise software supporting one or more communication protocols associated with communications such that the network 530 or interface's hardware is operable to communicate physical signals within and outside of the illustrated computer 502.

The computer 502 includes a processor 505. Although illustrated as a single processor 505 in FIG. 5, two or more processors may be used according to particular needs, desires, or particular implementations of the computer 502. Generally, the processor 505 executes instructions and manipulates data to perform the operations of the computer 502. Specifically, the processor 505 executes the functionality for predicting geochemical water elements GWEs in a water sample.

The computer 502 also includes a memory 506 that holds data for the computer 502 and/or other components that can be connected to the network 530 (whether illustrated or not). For example, memory 506 can be a database storing GWA water analysis data, and/or data consistent with this disclosure. Although illustrated as a single memory 506 in FIG. 5, two or more memories may be used according to particular needs, desires, or particular implementations of the computer 502 and functionality to predict geochemical water elements GWEs in a water sample. While memory 506 is illustrated as an integral component of the computer 502, in alternative implementations, memory 506 can be external to the computer 502 and/or the Safety KPI system 100.

The application 507 is an algorithmic software engine providing functionality according to particular needs, desires, or particular implementations of the computer 502, particularly with respect to functionality required for predicting geochemical water elements GWEs in a water sample. For example, application 507 can serve as one or more components, modules, applications, etc. (e.g., the above described G-WAST application) described with respect to any of the figures. Further, although illustrated as a single application 507, the application 507 may be implemented as multiple applications 507 on the computer 502. In addition, although illustrated as integral to the computer 502, in alternative implementations, the application 507 can be external to the computer 502.

There may be any number of computers 502 associated with, or external to, a computer system containing computer 502, each computer 502 communicating over network 530. Further, the terms "client," "user," and other appropriate terminology may be used interchangeably as appropriate without departing from the scope of this disclosure. Moreover, this disclosure contemplates that many users may use one computer 502, or that one user may use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, i.e., one or more modules of computer program instructions encoded on a tangible, non-transitory computer-storage medium for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be or further include special purpose logic circuitry, e.g., a central processing unit (CPU), an FPGA (field programmable gate array), or an ASIC (application-specific integrated circuit). In some implementations, the data processing apparatus and/or special purpose logic circuitry may be hardware-based and/or software-based. The apparatus can optionally include code that creates an execution environment for computer programs, e.g., code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, IOS or any other suitable conventional operating system.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, libraries, and such, as appropriate. Conversely, the features and functionality of various components can be combined into single components as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a global positioning system (GPS) receiver, or a portable storage device, e.g., a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, e.g., erasable programmable read-only memory (EPROM), electrically erasable programmable read-only memory (EEPROM), and flash memory devices; magnetic disks, e.g., internal hard disks or removable disks; magneto-optical disks; and CD-ROM, DVD+/−R, DVD-RAM, and DVD-ROM disks. The memory may store various objects or data, including caches, classes, frameworks, applications, backup data, jobs, web pages, web page templates, database tables, repositories storing business and/or dynamic information, and any other appropriate information including any parameters, variables, algorithms, instructions, rules, constraints, or references thereto. Additionally, the memory may include any other appropriate data, such as logs, policies, security or access data, reporting files, as well as others. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube), LCD (liquid crystal display), LED (Light Emitting Diode), or plasma monitor, for displaying information to the user and a keyboard and a pointing device, e.g., a mouse, trackball, or trackpad by which the user can provide input to the computer. Input may also be provided to the computer using a touchscreen, such as a tablet computer surface with pressure sensitivity, a multi-touch screen using capacitive or electric sensing, or other type of touchscreen. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These and other UI elements may be related to or represent the functions of the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of wireline and/or wireless digital data communication, e.g., a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n and/or 802.20, all or a portion of the Internet, and/or any other communication system or systems at one or more locations. The network may communicate with, for example, Internet Protocol (IP) packets, Frame Relay frames, Asynchronous Transfer Mode (ATM) cells, voice, video, data, and/or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware and/or software, may interface with each other and/or the interface using an application programming interface (API) and/or a service layer. The API may include specifications for routines, data structures, and object classes. The API may be either computer language-independent or -dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API and/or service layer may be an integral and/or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking and/or parallel processing may be advantageous and performed as deemed appropriate.

Moreover, the separation and/or integration of various system modules and components in the implementations described above should not be understood as requiring such separation and/or integration in all implementations, and it should be understood that the described program components and systems can generally be integrated together in a single software product or packaged into multiple software products.

Accordingly, the above description of example implementations does not define or constrain this disclosure. Other changes, substitutions, and alterations are also possible without departing from the spirit and scope of this disclosure.

What is claimed is:

1. A computer-implemented method, comprising:
   collecting a first wellhead fluid sample from a petroleum well;
   performing multiple geochemical water analysis (GWA) tests to determine physical properties of and one or more geochemical water element (GWE) concentration values associated with the first wellhead fluid sample to form GWA water analysis data;
   determining correlation data associated with the GWA water analysis data;
   collecting a second wellhead fluid sample from the petroleum well;
   performing only a water conductivity analysis on the second wellhead fluid sample to determine water conductivity data;
   determining a current GWE value for a particular GWE of the second wellhead fluid sample using the determined correlation data and the determined water conductivity data; and
   in response to the determination and based on the determined water conductivity data, expanding or reducing development of a production field associated with a petroleum reservoir, wherein expanding the development of the production field comprises drilling one or more wellbores in the production field.

2. The computer-implemented method of claim 1, wherein the GWA water analysis data and a backup of the GWA water analysis data are stored into persistent memory storage.

3. The computer-implemented method of claim 1, wherein the GWA water analysis data includes at least one of pH, water specific gravity, conductivity, sodium (Na), calcium (Ca), magnesium (Mg), chloride (Cl), sulfate, carbonate, bicarbonate, or total dissolved solids (TDSs).

4. The computer-implemented method of claim 1, comprising using a geochemical water analysis statistical approach (G-WAST) application to determine correlations and relationships between the GWA water analysis data.

5. The computer-implemented method of claim 4, wherein the G-WAST application provides functionality to permit multiple selected data criteria to be considered together for illustration and calculations.

6. The computer-implemented method of claim 4, wherein an illustrated trendline can be manipulated to substantially fit within plotted data points of a scatterplot.

7. A non-transitory, computer-readable medium storing computer-readable instructions, the instructions executable by a computer and configured to:
   collect a first wellhead fluid sample from a petroleum well;
   perform multiple geochemical water analysis (GWA) tests to determine physical properties of and one or more geochemical water element (GWE) concentration values associated with the first wellhead fluid sample to form GWA water analysis data;
   determine correlation data associated with the GWA water analysis data;
   collect a second wellhead fluid sample from the petroleum well;
   perform only a water conductivity analysis on the second wellhead fluid sample to determine water conductivity data;
   determine a current GWE value for a particular GWE of the second wellhead fluid sample using the determined correlation data and the determined water conductivity data; and
   in response to the determination and based on the determined water conductivity data, expand or reduce development of a production field associated with a petroleum reservoir wherein expanding the development of the production field comprises drilling one or more wellbores in the production field.

8. The non-transitory, computer-readable medium of claim 7, wherein the GWA water analysis data and a backup of the GWA water analysis data are stored into persistent memory storage.

9. The non-transitory, computer-readable medium of claim 7, wherein the GWA water analysis data includes at least one of pH, water specific gravity, conductivity, sodium (Na), calcium (Ca), magnesium (Mg), chloride (Cl), sulfate, carbonate, bicarbonate, or total dissolved solids (TDSs).

10. The non-transitory, computer-readable medium of claim 7, comprising an instruction to use a geochemical water analysis statistical approach (G-WAST) application to determine correlations and relationships between the GWA water analysis data.

11. The non-transitory, computer-readable medium of claim 10, wherein the G-WAST application provides functionality to permit multiple selected data criteria to be considered together for illustration and calculations.

12. The non-transitory, computer-readable medium of claim 10, wherein an illustrated trendline can be manipulated to substantially fit within plotted data points of a scatterplot.

13. A system, comprising:
a memory;
a hardware processor interoperably coupled with the memory and configured to:
  collect a first wellhead fluid sample from a petroleum well;
  perform multiple geochemical water analysis (GWA) tests to determine physical properties of and one or more geochemical water element (GWE) concentration values associated with the first wellhead fluid sample to form GWA water analysis data;
  determine correlation data associated with the GWA water analysis data;
  collect a second wellhead fluid sample from the petroleum well;
  perform only a water conductivity analysis on the second wellhead fluid sample to determine water conductivity data;
  determine a current GWE value for a particular GWE of the second wellhead fluid sample using the determined correlation data and the determined water conductivity data; and
  in response to the determination and based on the determined water conductivity data, expand or reduce development of a production field associated with a petroleum reservoir, wherein expanding the development of the production field comprises drilling one or more wellbores in the production field.

14. The system of claim 13, wherein the GWA water analysis data and a backup of the GWA water analysis data are stored into persistent memory storage.

15. The system of claim 13, wherein the GWA water analysis data includes at least one of pH, water specific gravity, conductivity, sodium (Na), calcium (Ca), magnesium (Mg), chloride (Cl), sulfate, carbonate, bicarbonate, or total dissolved solids (TDSs).

16. The system of claim 13, configured to use a geochemical water analysis statistical approach (G-WAST) application to determine correlations and relationships between the GWA water analysis data.

17. The system of claim 16, wherein the G-WAST application provides functionality to permit multiple selected data criteria to be considered together for illustration and calculations, and wherein an illustrated trendline can be manipulated to substantially fit within plotted data points of a scatterplot.

* * * * *